(12) United States Patent
Hayano

(10) Patent No.: US 8,115,916 B2
(45) Date of Patent: Feb. 14, 2012

(54) SURFACE INSPECTING METHOD AND SURFACE INSPECTING APPARATUS

(75) Inventor: Fuminori Hayano, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/901,374

(22) Filed: Oct. 8, 2010

(65) Prior Publication Data

US 2011/0026017 A1    Feb. 3, 2011

Related U.S. Application Data

(63) Continuation of application No. PCT/JP2009/057232, filed on Apr. 8, 2009.

(30) Foreign Application Priority Data

Apr. 9, 2008    (JP) ................................ 2008-101367

(51) Int. Cl.
     *G01N 21/00*      (2006.01)
(52) U.S. Cl. .................................. 356/237.5; 356/237.4
(58) Field of Classification Search ..... 356/237.1–237.6
See application file for complete search history.

(56) References Cited

U.S. PATENT DOCUMENTS

| | | |
|---|---|---|
| 2004/0239918 A1 | 12/2004 | Sugihara et al. |
| 2005/0088665 A1 | 4/2005 | Bischoff et al. |
| 2006/0232769 A1 | 10/2006 | Sugihara et al. |
| 2007/0177136 A1 | 8/2007 | Nakano et al. |
| 2008/0013107 A1 | 1/2008 | Chard et al. |

FOREIGN PATENT DOCUMENTS

| | | |
|---|---|---|
| CN | 1758022 A | 4/2006 |
| JP | 06-043111 | 2/1994 |
| JP | 2001-185701 A | 7/2001 |
| JP | 2004-294194 A | 10/2004 |
| JP | 2006-105951 A | 4/2006 |
| JP | 2006-319121 A | 11/2006 |
| JP | 2007-510312 A | 4/2007 |
| JP | 2007-192759 | 8/2007 |
| JP | 2007-287794 A | 11/2007 |
| JP | 2008-022005 A | 1/2008 |
| JP | 2008-058248 A | 3/2008 |
| WO | WO 2005/043600 A2 | 5/2005 |

*Primary Examiner* — Gregory J Toatley
*Assistant Examiner* — Tri T Ton
(74) *Attorney, Agent, or Firm* — Miles & Stockbridge PC

(57) ABSTRACT

Provided is a surface inspecting method for inspecting a surface of a semiconductor substrate having linear line patterns repeatedly arranged and hole-shaped hole patterns formed on the line patterns. The surface inspecting method includes setting inspecting conditions; irradiating the surface of the semiconductor substrate with illumination light under the set inspecting conditions; detecting diffracted light from the semiconductor substrate irradiated with illumination light; and judging existence/nonexistence of a defect in the hole patterns, based on the detected diffracted light. The inspecting conditions are to be set so that the irradiating direction of the illumination light on the surface of the semiconductor substrate is different from the repeated arrangement direction of the line patterns and substantially matches the repeated arrangement direction of the hole patterns.

20 Claims, 37 Drawing Sheets

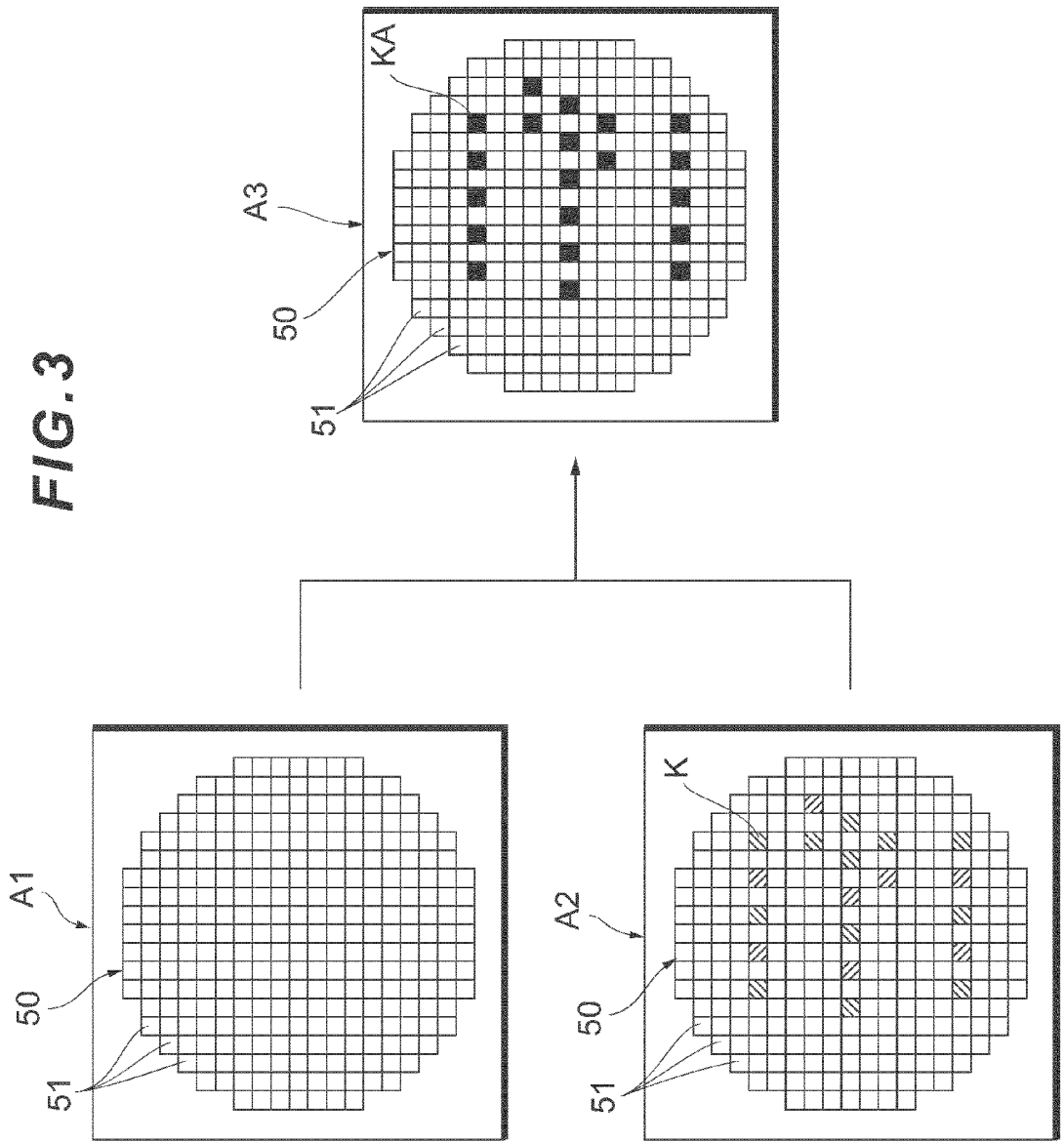

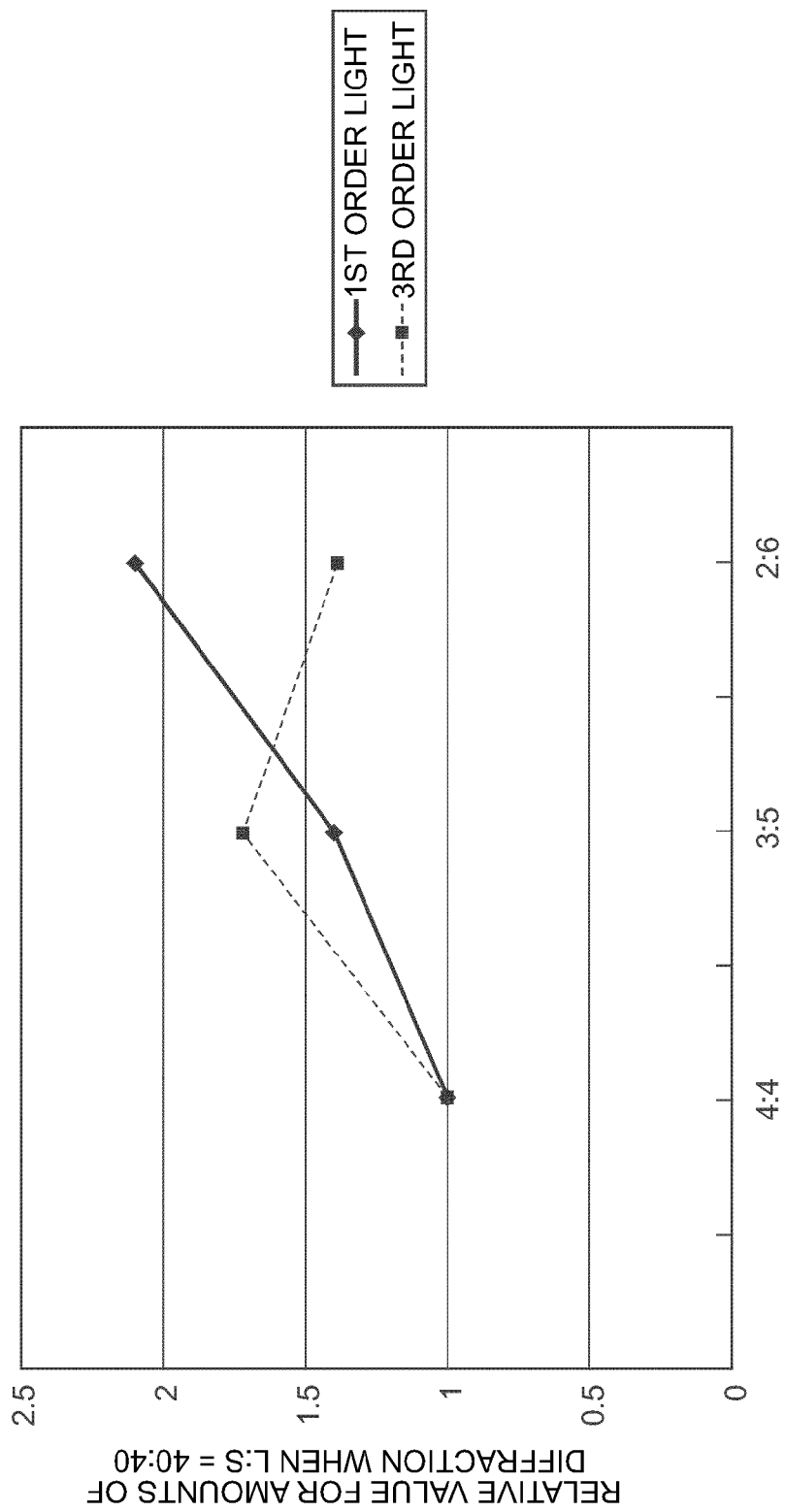

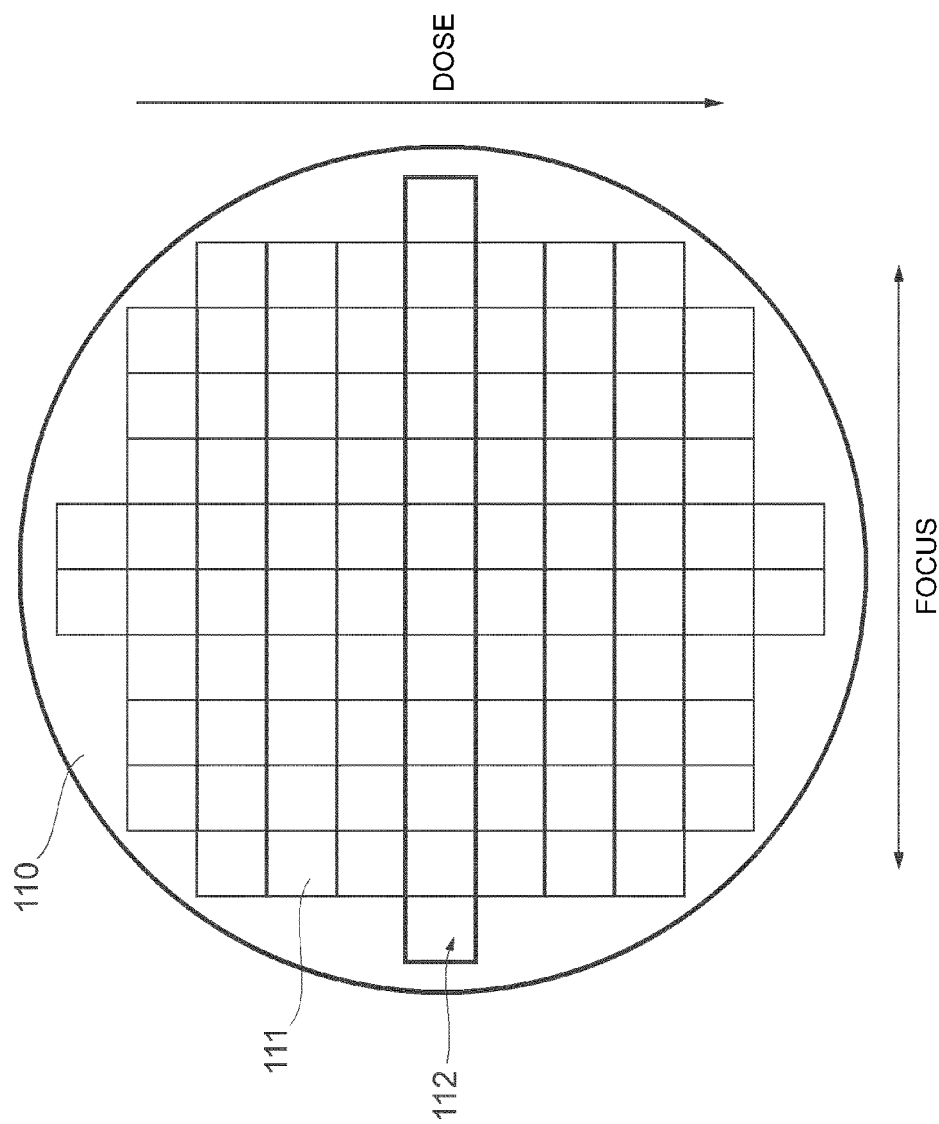

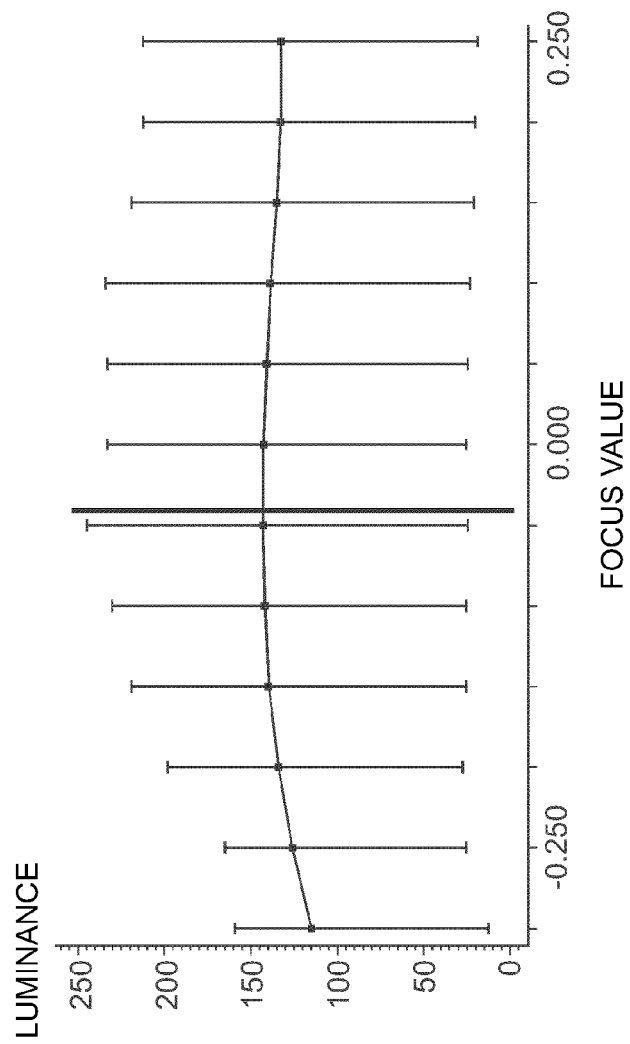
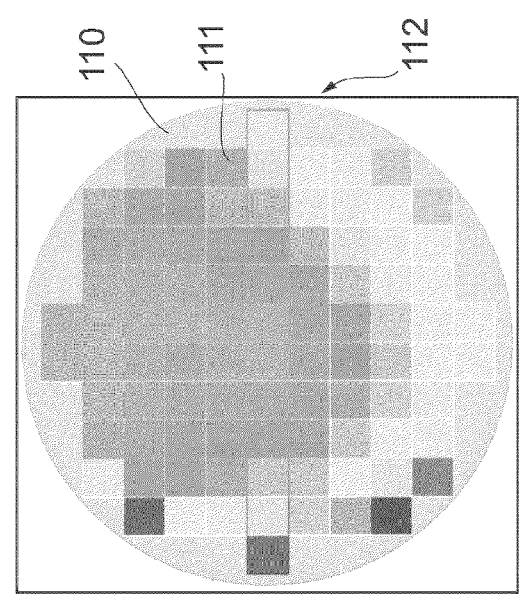
FIG. 18A
FIG. 18B

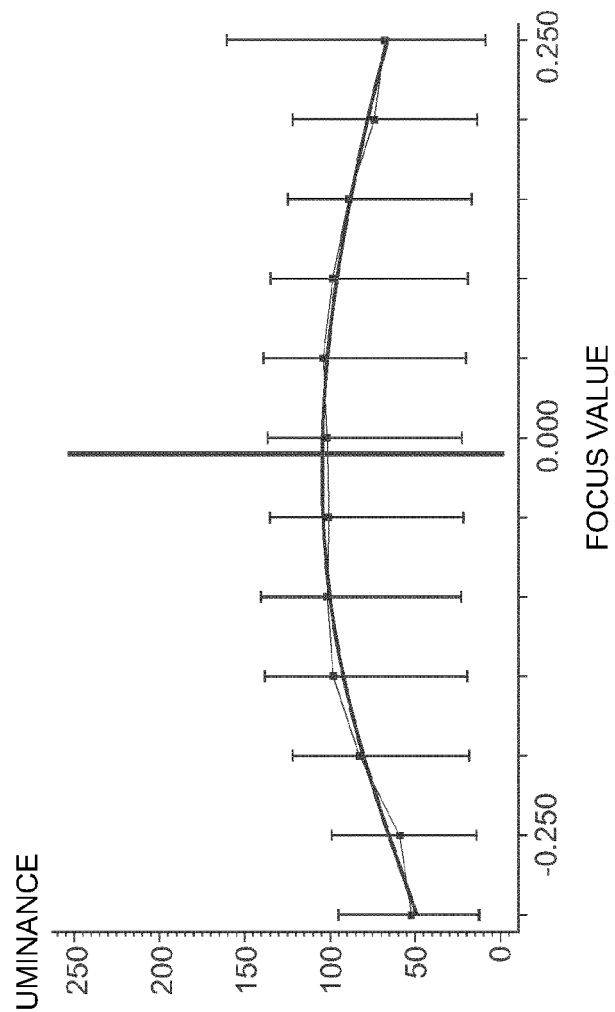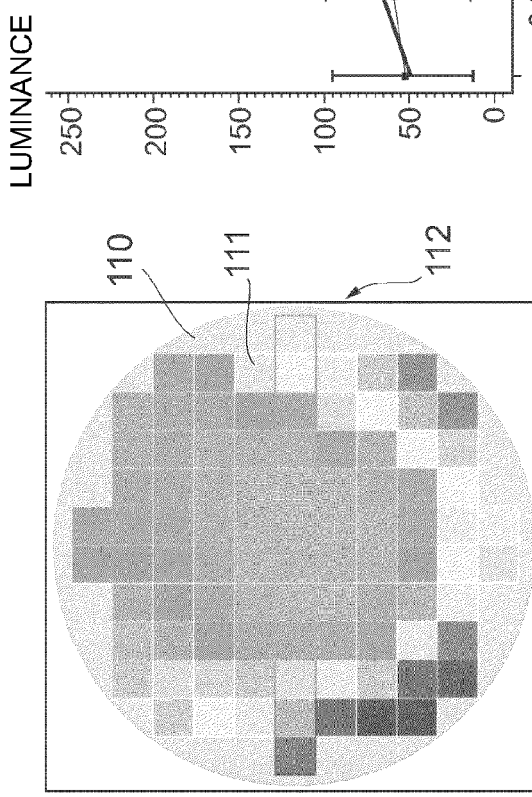
FIG.19A
FIG.19B

SURFACE INSPECTING METHOD AND SURFACE INSPECTING APPARATUS

This is a continuation of PCT International Application No. PCT/JP2009/057232, filed on Apr. 8, 2009, which is hereby incorporated by reference. This application also claims the benefit of Japanese Patent Application No. 2008-101367, filed in Japan on Apr. 9, 2008, which is hereby incorporated by reference.

TECHNICAL FIELD

The present invention relates to a surface inspecting method and surface inspecting apparatus to inspect a surface of a wafer or the like in a semiconductor manufacturing process.

TECHNICAL BACKGROUND

As a semiconductor device, a memory element such as a DRAM (Dynamic Random Access Memory), a flash memory (storage device) and a device called a logic element having a storing section and a processing section are available. In recent years, a pattern for a semiconductor device tends to become increasingly fine and minute due to a trend of high speed processing, less power consumption, and increased storage capacity and, therefore, a demand for inspection of a defect occurring in a manufacturing process of semiconductor devices becomes severer at the same time. A defocus defect occurring in the exposure process in particular is a largest factor of defective products. The defocus defect refers to swelling of a wafer surface caused by foreign matters existing between a rear surface of a semiconductor wafer and a wafer stage which occurs at time of an exposure process and, as a result, a pattern line width and/or pattern diameter value being called a CD (Critical Dimension) value is out of dimensional tolerance resulting in pattern defects. Moreover, in a scanning-type exposure machine in particular, a focus change occurs in an exposure shot due to a focusing error which causes the CD value to be out of tolerance, also resulting in a defect in a pattern.

As an apparatus to automatically inspect a defocus defect, an apparatus to detect a defect in a pattern has been in practical use which is configured to irradiate a surface of a semiconductor wafer with illumination light to receive diffracted light from a repeating pattern on the surface of the wafer and to utilize a change in an amount of diffracted light occurring in the diffracted light from a defective portion (the change occurs due to difference in CD values) (see, for example, Patent Reference 1). The diffracted light is produced from a pattern of a repeating arrangement and its state depends on repeatability (cycle called an arrangement or a pitch). As a semiconductor device is becoming increasingly fine and minute, a repeating cycle of the repeating pattern (pitch) naturally becomes smaller and, in a memory device such as a DRAM, a transistor and/or capacitor has to be disposed in a small cell area and the arrangement of a repeating pattern (hole pattern) of a hole called a contact hole including a bit contact, capacitor contact (or called a storage node contact), cylinder contact (storage capacitor) and the like in one cell is two dimensional. Then, one cell further has an arrangement repeated two-dimensionally and, therefore, most of the surface of a memory device is occupied by two-dimensional repeating patterns.

CITATION LIST

Patent Document

Patent Reference 1: Japanese Laid-Open Patent Publication No. 2006-105951

SUMMARY OF THE INVENTION

Problems to be Solved by the Invention

When such the inspection apparatus to inspect a hole pattern is used, as in the case of the inspection of a linear repeating pattern (line pattern), due to a reason that many patterns have repeatability in 0 or 90 degree direction, an attempt to find out diffraction condition out for these two azimuth angles has been made. However, such inspecting conditions are not always the optimum conditions for the inspection of a hole pattern.

The present invention has been made in light of problems described above and has an object to provide a surface inspecting method and surface inspecting apparatus which enable the inspection of a hole pattern according to the most optimized inspecting conditions.

Means to Solve the Problems

To achieve such an object, a surface inspecting method of the 1st invention is the method for inspecting a surface of a semiconductor substrate having a line pattern and a hole pattern formed on the line pattern, each being arranged repeatedly including a first step of setting an irradiating direction of illumination light on a surface of the semiconductor substrate, a second step of irradiating the surface of the semiconductor substrate with illumination light from the irradiating direction set at the first step, a third step of detecting diffracted light corresponding to a pitch of the hole pattern from the surface irradiated with the illumination light, and a fourth step of judging existence/non-existence of a defect occurring in the hole pattern based on the diffracted light detected at the third step and in the first step, the irradiating direction being set so that the irradiating direction of the illumination light on the surface of the semiconductor substrate is different from a repeating arrangement direction of the line pattern and substantially matches a repeating arrangement direction of the hole pattern.

It is preferable that, in the first step of the above surface inspecting method, the irradiating direction is set so that the irradiating direction of the illumination light on the surface of the semiconductor substrate is different from the repeating arrangement direction of the line pattern and the diffracted light an amount of which greatly changes depending on a change in a shape of the hole pattern occurs.

It is preferable that, in the first step of the surface inspecting method, the irradiating direction is set by performing simulation of a change in an amount of the diffracted light according to a change in shape of the hole pattern based on one of designing information of the hole pattern and shape measurement information of a hole pattern whose shape has been measured in advance.

A surface inspecting method of the second invention is the method for inspecting a surface of a semiconductor substrate having a hole-shaped pattern including a first step of setting an irradiating direction of an illumination light to be applied to a surface of the semiconductor substrate, a second step of irradiating the surface of the semiconductor substrate with illumination light from the irradiating direction set at the first step, a third step of detecting diffracted light corresponding to a pitch of the hole pattern from the surface irradiated with the illumination light, and a fourth step of judging existence/non-existence of a defect in the hole pattern based on the diffracted light detected at the third step, wherein, in the first step, the irradiating direction is set by performing simulation of a change in an amount of diffracted light according to a change in shape of the hole pattern so that the diffracted light an amount of which changes greatly according to a change in shape of the hole pattern occurs.

It is preferable that, in the first step of the surface inspecting method, simulation of a change in an amount of the diffracted light is performed according to a change in shape of the hole pattern based on one of designing information about the hole pattern and shape measurement information about a hole pattern whose shape has been measured in advance.

It is preferable that, in the first step of the surface inspecting method, the irradiating direction is set so that the diffracted light an amount of which changes greatly according to a change in shape of the hole pattern occurs and that diffracted light is not easily produced form a layer on a side being lower than the hole pattern.

A surface inspecting apparatus of the first invention is the apparatus for inspecting a surface of a semiconductor substrate having a line pattern and a hole pattern formed on the line pattern, including a setting section to set an irradiating direction of illumination light to be applied to a surface of the semiconductor substrate, an illuminating section to irradiate the surface of the semiconductor substrate with illumination light in the irradiating direction set by the setting section, and a detecting section to detect diffracted light corresponding to a pitch of the hole pattern from the surface irradiated with the illumination light, and an inspecting section which judges existence/non-existence of a defect occurring in the hole pattern based on the diffracted light detected by the inspecting section, wherein the setting section sets the irradiating direction so that the irradiating direction of the illumination light on the surface of the semiconductor substrate is different from a repeating arrangement direction of the line pattern and substantially matches a repeating arrangement direction of the hole pattern.

It is preferable that, in the surface inspecting apparatus, the setting section sets the irradiating direction so that the irradiating direction of the illumination light on the surface of the semiconductor substrate is different from the repeating arrangement direction of the line pattern and the diffracted light an amount of which greatly changes depending on a change in a shape of the hole pattern occurs.

It is preferable that, in the surface inspecting apparatus according, the setting section sets the irradiating direction by performing simulation of a change in an amount of the diffracted light according to a change in shape of the hole pattern based on one of designing information about the hole pattern and shape measurement information about a hole pattern whose shape has been measured in advance.

A surface inspecting apparatus of the second invention is an apparatus for inspecting a surface of a semiconductor substrate having a hole pattern, including a setting section to set an irradiating direction of an illumination light to be applied to a surface of the semiconductor substrate, an illuminating section to irradiate a surface of the semiconductor substrate with illumination light from the irradiating direction set by the setting section, a detecting section to detect diffracted light corresponding to a pitch of the hole pattern from the surface irradiated with the illumination light, and an inspecting section to judge existence/non-existence of a defect in the hole pattern based on the diffracted light detected by the detecting section, wherein the setting section sets the irradiating direction by performing simulation of a change in an amount of diffracted light according to a change in shape of the hole pattern so that the diffracted light an amount of which changes greatly according to a change in shape of the hole pattern occurs.

It is preferable that, in the surface inspecting apparatus, the setting section performs simulation of a change in an amount of the diffracted light according to a change in shape of the hole pattern based on one of designing information about the hole pattern and shape measurement information about a hole pattern whose shape has been measured in advance.

It is preferable that, in the surface inspecting apparatus, the setting section sets the irradiating direction so that the diffracted light an amount of which changes greatly according to a change in shape of the hole pattern occurs and that diffracted light is not easily produced form a layer on a side being lower than the hole pattern.

Advantageous Effects of the Invention

According to the present invention, a hole pattern can be inspected according to the optimum inspecting conditions.

BRIEF DESCRIPTION OF THE DRAWINGS

FIG. 3 is a schematic diagram showing a wafer image.

FIG. 16 is a graph showing a relation between duty and a change in an amount of diffracted light.

FIG. 17 is a plan view of an FEM (Focus Exposure Matrix) wafer.

FIGS. 18A and 18B are diagrams showing one example of a luminance map.

FIGS. 19A and 19B are diagrams showing one example of a luminance map.

DESCRIPTION OF THE EMBODIMENTS

Figure 1:
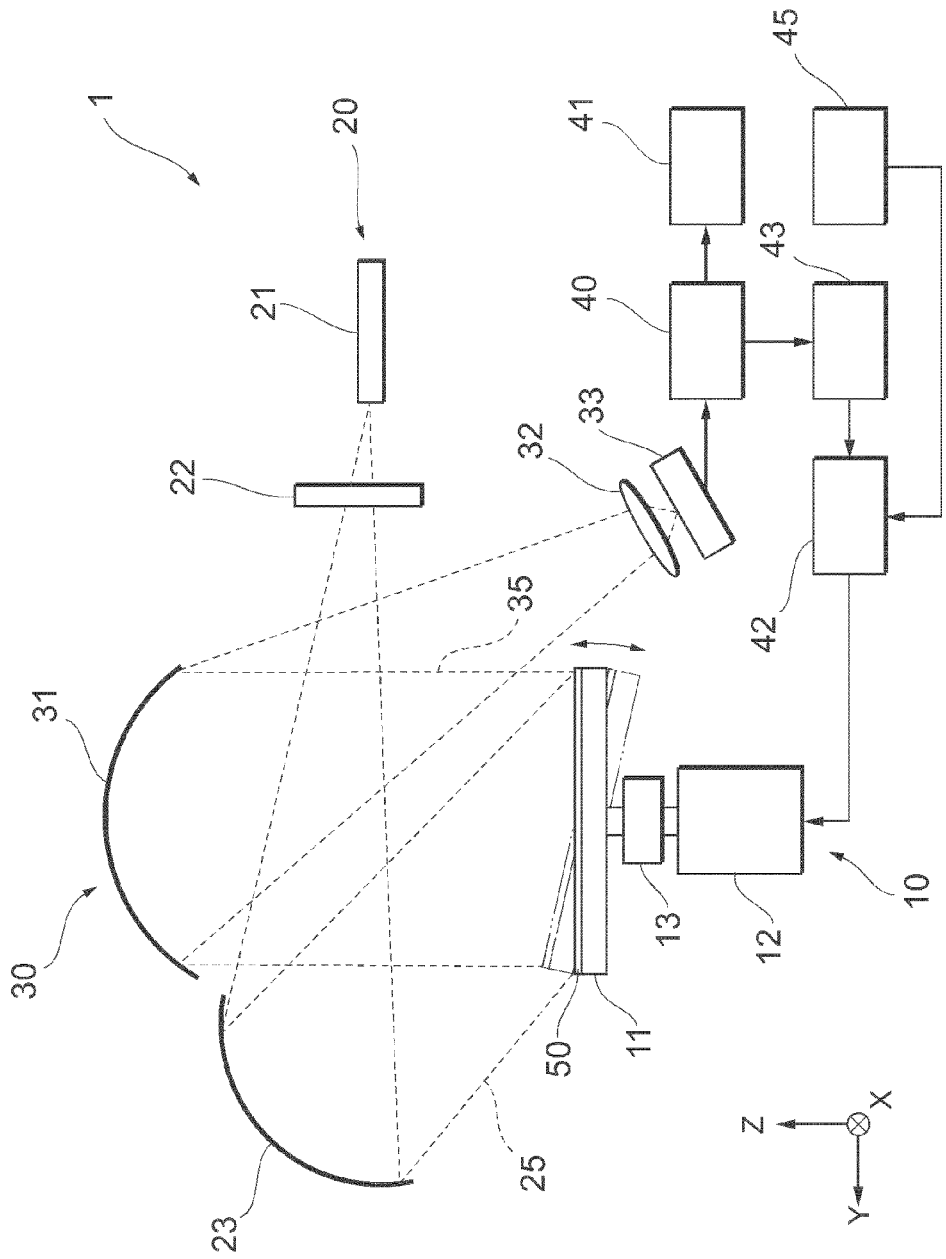
FIG. 1 is a diagram showing an entire configuration of the surface inspection apparatus of the present invention.

Hereinafter, a preferred embodiment of the present invention is described by referring to drawings. The surface inspecting apparatus 1 of the present embodiment is shown in FIG. 1 and mainly includes a wafer holding section 10, an illuminating section 20, a detecting section 30, an image processing section 40, an inspecting section 41, an inspecting condition setting section 42, an FEM evaluating section 43, and an inspecting condition determining section 45. Moreover, in the present embodiment, the direction perpendicular to the paper surface of FIG. 1 is defined as an X direction, a horizontal direction is defined as a Y direction, a vertical direction is defined as a Z direction, and a rotational direction in an XY plane is defined as a θ direction.

The wafer holding section 10 has a stage 11 on which a semiconductor wafer 50 (hereinafter, simply the wafer 50) is put, a θ rotating section 12 to rotate the stage 11 in the θ direction, and a tilting section 13 to tilt the stage 11. The stage 11 holds, by vacuum adsorption or the like, the wafer 50 put on an upper surface of the stage 11 by using an unillustrated conveying apparatus. The stage 11 holding the wafer 50 can be rotated in the θ direction using an axis adapted to pass through the center of the wafer 50 (center of the stage 11) and to be perpendicular to the surface of the wafer 50 as a rotational axis. Also, the stage 11 is so configured to be tiltable, by the tilting section 13, about the axis (axis parallel to the X direction) passing through the surface of the wafer 50 and to adjust the incident (and outgoing) angle of the illumination light 25.

The illuminating section 20 has a light source 21, a wavelength selecting section 22, and an illuminated mirror 23 and is configured so as to irradiate a surface of the wafer 50 with illumination light 25. As the light source 21, a mercury lamp is used. Therefore, the light emitted from the light source 21 contains a plurality of rays of light each having a wavelength λ, for example, an e-line (λ=546 nm), g-line (λ=436 nm), h-line (λ=405 nm), j-line (λ=313 nm), and a ray having the wavelength λ of about 250 nm and only the ray of light having a specified wavelength out of these rays of light is selected by a wavelength selecting section 22 so as to be allowed to transmit through the wavelength selecting section 22. The light transmitted through the wavelength selecting section 22 is reflected by the illuminated mirror 23 to become collimated flux which serves as the illumination light 25 to illuminate the wafer 50. The illumination light 25 becomes light having a wavelength of monochromatic light at the wavelength selecting section 22 and becomes collimated flux at the illuminated mirror 23 and, therefore, parallel rays of the diffracted light 35 are produced from a repeating arrangement pattern of the wafer 50.

The detecting section 30 for detecting the diffracted light 35 from the wafer 50 is so configured to have a light receiving mirror 31, a light receiving lens 32, and a photography section 33. The rays of the diffracted light 35, after being gathered by the light receiving mirror 31, reach a photographic surface of the photography section 33 through the light receiving lens 32 and forms an image of the wafer 50 on the photographic surface. As a result, the image of the surface of the wafer 50 is formed on the photographic surface of the photography section 33. The photography section 33 photoelectrically converts the image of the surface of the wafer 50 formed on the photographic surface to generate image signals and outputs the image signals to the image processing section 40. By configuring as above, the image of the surface (all surfaces) of the wafer 50 can be collectively photographed and, therefore, scanning of the surface of the wafer 50 is not required, thus enabling the surface of the wafer 50 to be inspected at high speed.

As shown in FIG. 3, the image processing section 40, based on the image signals of the wafer 50 inputted from the photography section 33, converts the image of the wafer 50 into a digital image with specified bits (for example, 8 bits). The image processing section 40 stores the image A1 of a non-defective wafer (wafer having no defects) into an unillustrated data base in order to use the image A1 as a template and then compares the image A1 with the inspected image A2 of the wafer 50 to be inspected, which is obtained through the photographic process by using the photography section 33. At this point of time, on the wafer 50 having a defect, an amount of diffracted light changes only in a portion of the defect K. Therefore, the inspecting section 41 connected electrically to the image processing section 40 makes a judgment about whether there is a defect based on the result from the comparison (change in the amount of diffracted light) between the inspected image A2 and non-defective wafer image A1. As a result, when it is judged by the inspecting section 41 that there is a defect on the surface of the wafer 50, a defect judged image A3 showing a region kA of a shot 51 containing the defect in a highlighted manner, out of a plurality of shots 51, 51, ... arranged on the surface of the wafer 50, is generated by the image processing section 40 and is displayed, together with the judgment result, on an unillustrated displaying section. Moreover, the image A1 of a non-defective wafer may be stored in a data base not only for every process for the wafer 50 but also for each of a plurality of inspecting conditions in the same process. Furthermore, the image data on the inspected image A2 can be outputted from the image processing section 40 to the FEM evaluating section 43 to calculate the average luminance of the inspected image A1 for every exposure shot, which is described later.

Figure 4A:
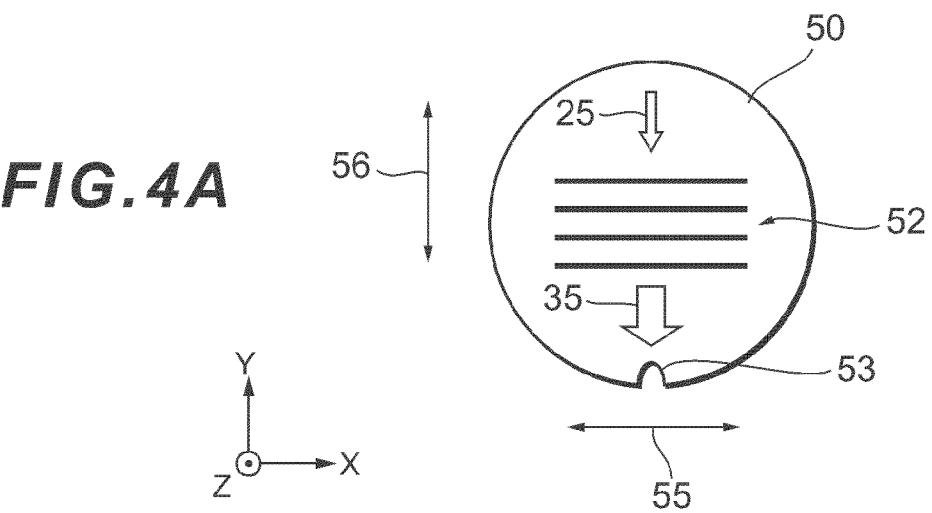
FIGS. 4A, 4B, and 4C are plan views of a wafer.

The inspecting condition setting section 42 makes the θ rotating section 12 and tilting section 13 set the stage 11 by rotating the stage 11 by θ degrees and by tilting the stage 11 so that the stage 11 has a specified azimuth (rotation angle θ of the stage 11 relative to a notch or the like) and a tilt angle (angle at which the stage 11 is tilted from a horizontal state) at which the diffracted light 35 can be detected. The relation between the repeated arrangement pattern to be formed on the surface of the wafer 50 and diffracted light 35 is explained by referring to FIGS. 4A to 4C. FIG. 4A is a plan view obtained when the wafer 50 is seen from its upper side, in which it is assumed that the wafer 50 is put in parallel to the XY plane. As shown in FIG. 4A, the illumination light 25 is incident to the wafer 50 in a slanted manner using the surface being parallel to the YZ plane as an incident surface. Then, it is assumed that the repeated arrangement pattern 52 formed on the surface of the wafer 50 is a simple line and space pattern. Moreover, the direction in which the repeated arrangement pattern 52 extends is defined as an arrangement direction 55 of the repeated arrangement pattern 52 and the direction being perpendicular to the arrangement direction is defined a repeating direction 56 of the repeated arrangement pattern 52.

Figure 4B:
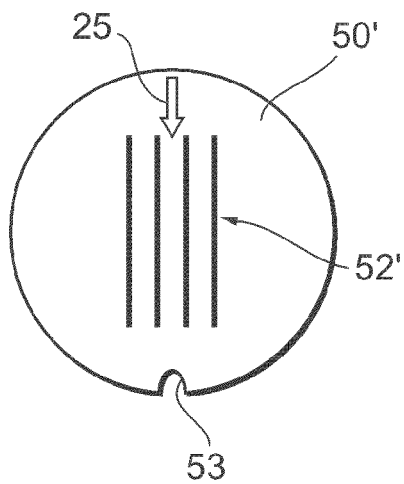
Figure 4C:
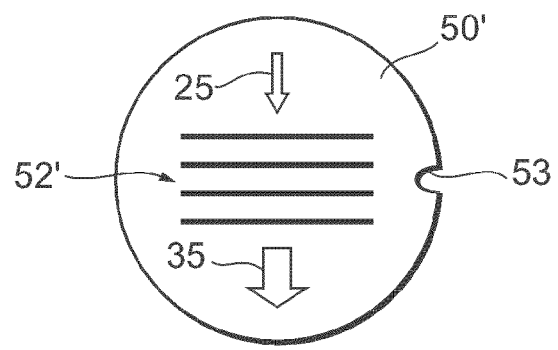

In the case of FIG. 4A, the arrangement direction 55 is the X direction and the repeating direction 56 is the Y direction and, therefore, the diffracted light 35 is produced within a surface being parallel to the YZ plane. On the other hand, as shown in FIG. 4B, in the case of a repeated arrangement pattern 52' in which the repeating direction is the X direction, while the illumination light 25 is incident to the wafer 50 in a slanted manner using the surface being parallel to the YZ plane as an incident surface, the diffracting light is not produced in the surface being parallel to the YZ plane. However, as shown in FIG. 4C, when the wafer 50 held by the stage 11 is rotated by θ (90) degrees (relative to the notch 53) by using the θ rotating section 12, the repeating direction of the repeated arrangement pattern 52' becomes the Y direction and, therefore, the diffracted light 35 is produced within a surface being parallel to the YZ plane.

As shown in FIG. 1, since the optical system (illumination system 20) applying the illumination light 25, together with the optical system (detecting section 30) detecting the diffracted light 35, is disposed within a surface being parallel to the YZ plane, through the θ rotation of the wafer 50 by the θ rotating section 12, regardless of the direction of the repeated arrangement pattern, the stage 11 can be set at any azimuth angle at which the diffracted light can be received. On the other hand, in the case of the diffracted light to be produced on a surface being parallel to the YZ plane, a diffraction angle (angle formed between the illumination light 25 and diffracted light 35) differs depending on a cycle period (pitch) of the repeated arrangement pattern 52. According to optical principles, the smaller the pitch becomes, the larger the diffraction angle of 1st order diffracted light becomes. Therefore, the inspecting condition setting section 42 allows the tilting section 13 to tilt the stage 11 (wafer 50) so that the diffracted light 35 can be reliably received by the light receiving mirror 31. Since the tilt angle can be calculated theoretically from the pitch of the repeated arrangement pattern 52 and the wavelength of the illumination light 25, if the repeating direction 56 of the repeated arrangement pattern (line and space pattern) 52 and the pitch are known, the inspecting condition determining section 45 can determine inspecting conditions such as a azimuth angle and/or tilt angle and can input these obtained conditions into the inspecting condition setting section 42 for setting.

Figure 2:
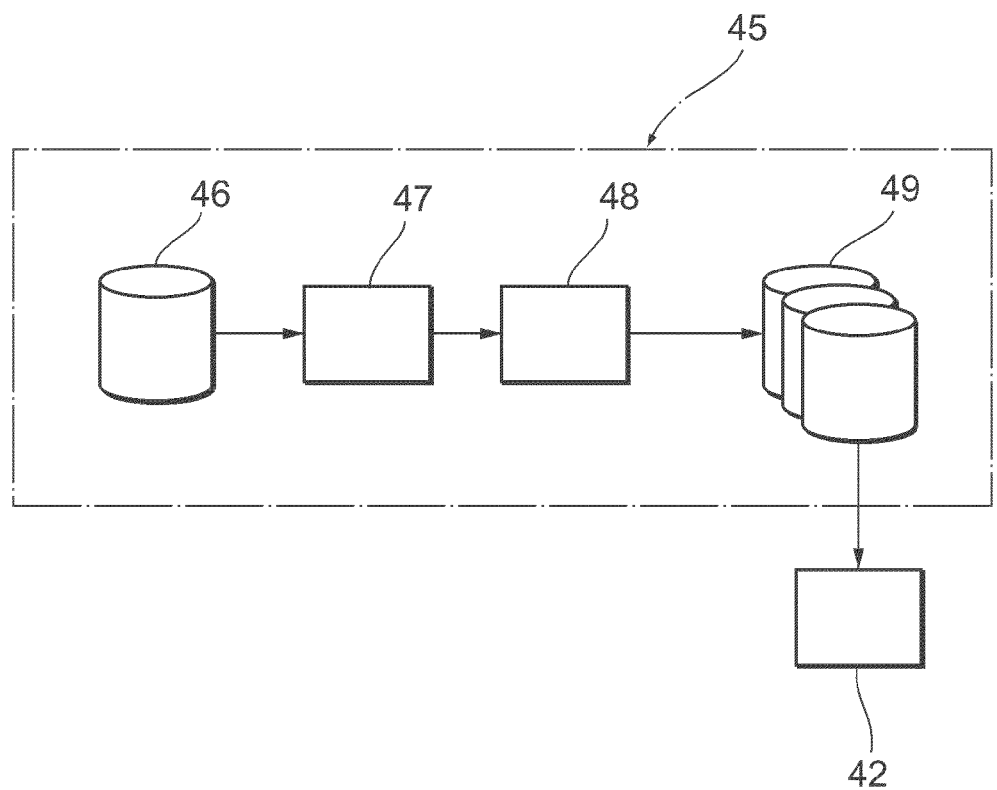
FIG. 2 is a control block diagram of an inspecting condition determining section.

As is understood from the above description, when the arrangement information is already known, the determination of inspecting conditions by the inspecting condition determining section 45 is easy. Next, the processing to be performed by the inspecting condition determining section 45 is described. As shown in FIG. 2, the inspecting condition determining section 45 is made up of an arrangement data inputting section 46, a CD value change converting section 47 connected electrically to the arrangement data inputting section 46, a diffracted light simulator section 48 connected electrically to the CD value change converting section 47, and an inspecting condition data outputting section 49 connected electrically to the diffracted light simulator section 48.

In the case shown in FIG. 4A, the arrangement direction 55 of the repeated arrangement pattern (line and space pattern) 52 is the X direction and the repeating direction 56 is the Y direction. Furthermore, if the repeating pitch is, for example, 0.2 μm and the ratio between a line and a space (hereinafter simply "duty") is 1:1, such arrangement information (information that the arrangement direction is the X direction, repeating direction is the Y direction, repeating pitch is 0.2 μm, duty is 1:1, and the like) is first inputted into the arrangement data inputting section 46 for being stored. The above arrangement information may be CAD (Computer Aided Design) data of a reticle, however, the surface inspecting apparatus 1 of the present embodiment is related to the defect inspection of the wafer 50 and, therefore, it is needless to say that the arrangement information is preferably a value being near the value obtained after the process of being exposure-transferred onto the wafer 50. For example, even when the duty is 1:1, the duty changes depending on whether an amount of exposure (dose) is large or small relative to a specified dose amount and, therefore, the arrangement information (duty) may be corrected by using a measured value of an actual SEM (Scanning Electron Microscope) or the like.

The CD value, which is a line width in the case of the line and space pattern and is a diameter of a hole in the case of the hole pattern, has necessarily a tolerance. Too slender line causes breakage and too thick line causes leakage current. The CD value is regulated from viewpoints that too small hole diameter induces contact failure and too large hole diameter induces leakage current. Therefore, in the CD value change converting section 47, a changed CD value obtained by changing the CD value is virtually set, for example, the CD value is set by using values within ±5%, ±10%, ±15%, ±20%, ±25%, and the like of a designed CD value calculated based on arrangement information stored in the arrangement data inputting section 46. Then, the CD value change converting section 47 inputs the designed CD value and changed CD value into the diffracted light simulator section 48. The diffracted light simulator section 48 (described later) basically determines inspecting conditions using FFT processing by which diffracted light is calculated by performing a simulation. Next, the diffracted light simulator section 48 outputs results from the processing as inspecting condition data which is then outputted to the inspecting condition setting section 45 through the inspecting condition data outputting section 49.

Next, manufacturing processes of the semiconductor wafer 50 (DRAM) to be inspected are described by referring to FIGS. 5 to 12. Moreover, details of manufacturing processes are disclosed in Japanese Laid-Open Patent Publication Nos. 2001-185701, 2006-319121, 2007-287794 and the like. In the present embodiment, only the important critical processes (process for higher device density) for the defect inspection by using a diffracted method is described.

Figure 5:
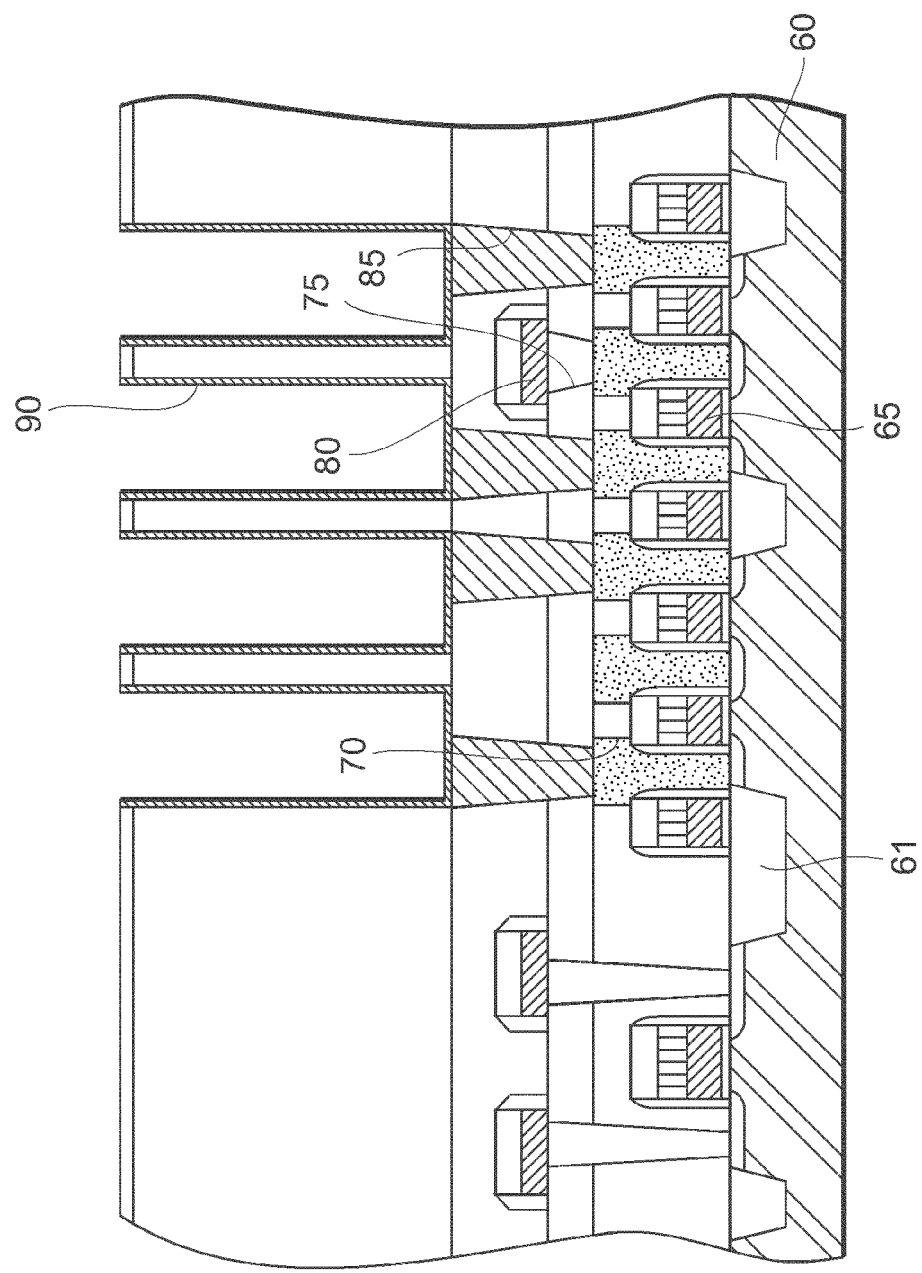
FIG. 5 is a partial cross-sectional view of a wafer.
Figure 6:
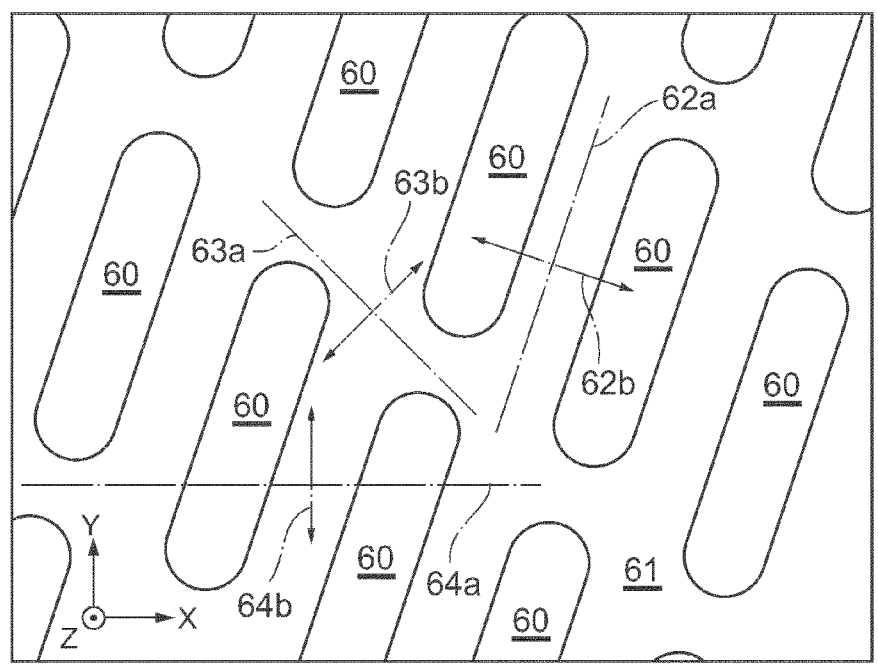
FIG. 6 is a schematic diagram showing a field process.

The field process, as shown in FIGS. 5 and 6, is a first critical process to form an active area 60 and a field (element separation region) 61. In the semiconductor wafer (DRAM) of F=90 nm or F=70 nm, the arrangement direction 62a of the active area 60 is tilted by 72 degrees relative to the X direction and the direction perpendicular to the arrangement direction 62a is the repeating direction 62b of the active area 60. In the present embodiment, F denotes a working dimension (that is, a half of the pitch of a gate or a word line). On the other hand, when the field 61 is noted, it can be thought that there is an arrangement direction 63a of 45 degree direction in a clearance between the active areas 60 arranged in the direction being tilted 72 degrees relative to the X direction and the direction perpendicular to the arrangement direction 63a is a repeating direction 63b. It can be also thought that there is an arrangement direction 64a in a clearance between the active areas 60 and the Y direction perpendicular to the arrangement direction 64a is a repeating direction 64b having a long cycle.

Figure 7:
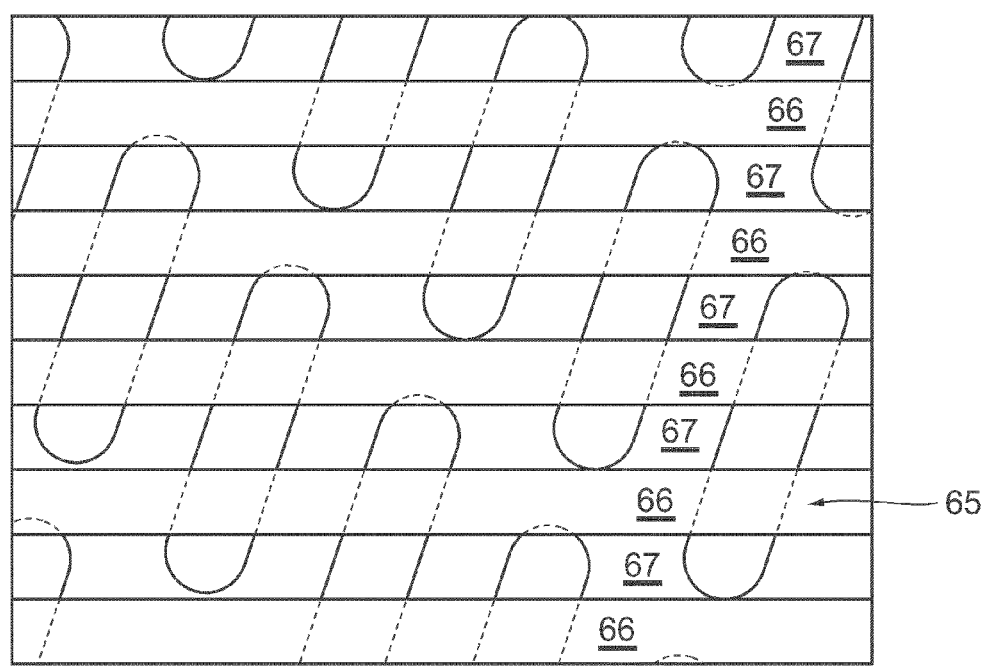
FIG. 7 is a schematic diagram showing a gate process.

After the completion of the field process, non-critical processes including 5 to 10 processes such as a doping process, ion implantation process, CVD (Chemical Vapor Deposition) process are performed and, then, the next gate process begins. The gate process, as shown in FIGS. 5 and 7, is a critical process of forming a gate 65 serving as a word line. The gate 65 is the line and space pattern and, in general, the duty between the line 66 and space 67 is 1:1. The arrangement direction of the gate 65 is the X direction and the repeating direction is the Y direction.

Figure 8:
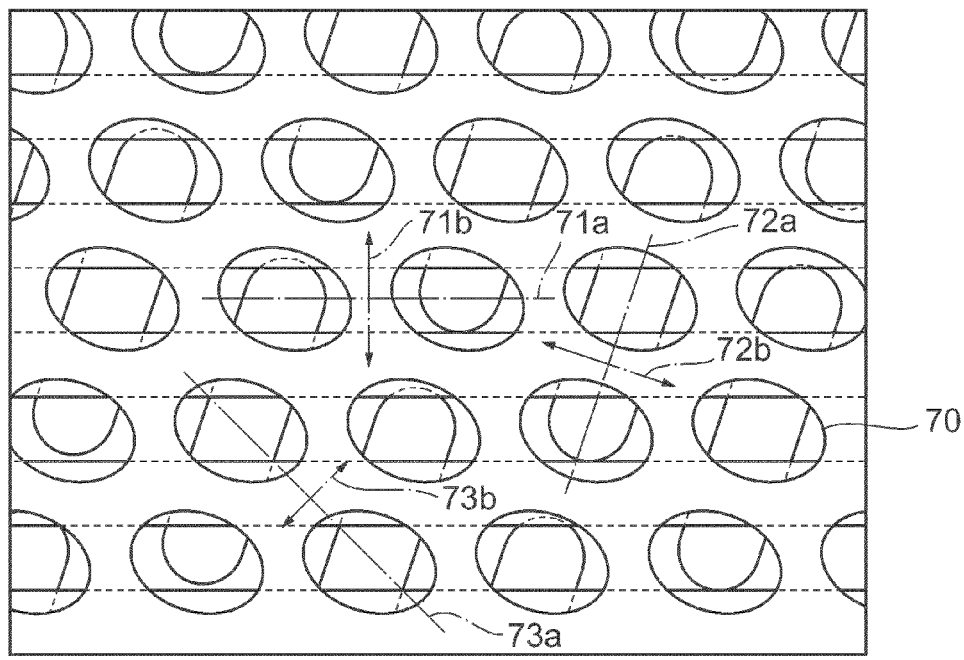
FIG. 8 is a schematic diagram showing a cell contact process.

After the completion of the gate process, non-critical processes including 5 to 10 processes such as a doping, ion implantation, CVD process, and the like are performed, and then transistors (not shown) are formed and then the next cell contact process is performed. The cell contact process, as shown in FIGS. 5 and 8, is a critical hole process with two aims of forming cell contacts (hole) 70 for the bit contact and capacitor contact. It can be said that, the critical hole process, out of the processes of manufacturing the DRAM, is the most dense and close process. In the cell contact 70, an arrangement direction 71a in the X direction, arrangement direction 72a in the 72 degree direction, arrangement direction 73a in the −45 degree direction can be easily found from FIG. 8 and each of the directions perpendicular to these is, respectively, a repeating direction 71b for the arrangement direction 71a in the X direction, repeating direction 72b for the arrangement direction 72a in the 72 degree direction, and the repeating direction 73b in the −45 degree direction. Moreover, though there may be other repeating arrangements and details are described by referring to FIG. 26. Furthermore, the cell contact 70 is connected at the position being offset from the position of the capacitor contact to be described later and, therefore, has an elliptical shape and its short diameter direction matches the arrangement direction 72a in the 72 degree direction.

Figure 9:
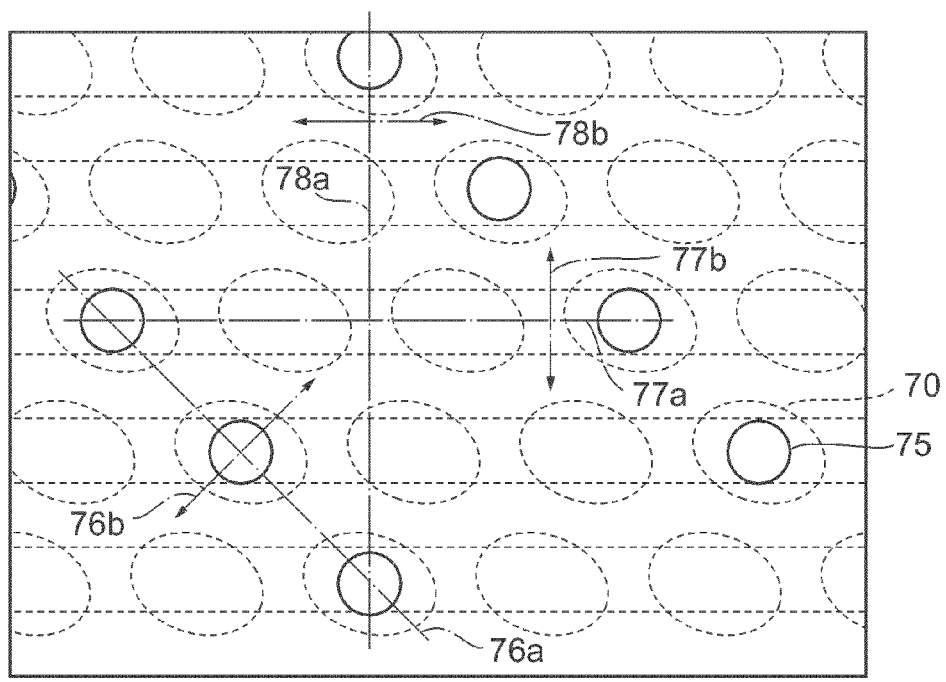
FIG. 9 is a schematic diagram showing a bit contact process.

The subsequent bit contact process, as shown in FIGS. 5 and 9, is a critical hole process of forming a bit contact 75 connected to the cell contact 70 and a bit line to be described. In the cell contact 75, an arrangement direction 76a in the −45 degree direction, arrangement direction 77a in the zero degree direction (X direction), arrangement direction 78a in the 90 degree (Y direction) direction can be easily found from FIG. 9 and each of the directions perpendicular to these is, respectively a repeating direction 76b for the arrangement direction 76a in the −45 degree direction, repeating direction 77b for the arrangement direction 77a in the zero degree direction (X direction), and repeating direction 78b for the arrangement direction 78a in the 90 degree direction (Y direction). Moreover, though there may be other repeating arrangements, details are described by referring to FIG. 20.

Figure 10:
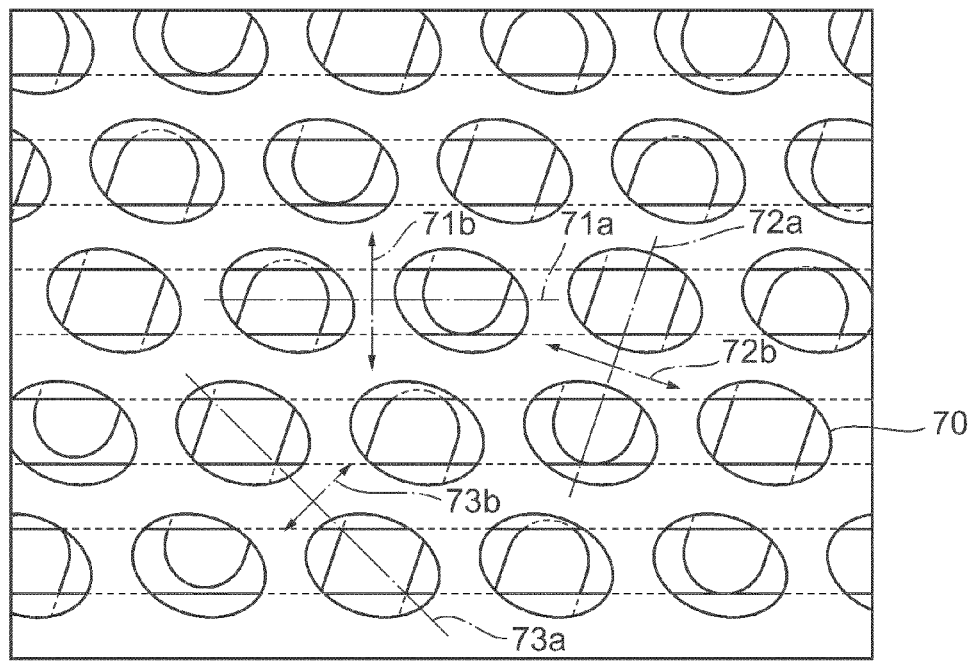
FIG. 10 is a schematic diagram showing a bit line process.

The subsequent bit line process, as shown in FIGS. 5 and 10, is a critical process of forming a bit line 80 orthogonal to the gate 65 (word line) to be connected to the bit contact 75. The arrangement direction of the gate 65 is the X direction (repeating direction is the Y direction) and, therefore, the arrangement direction of the bit line 80 is the Y direction (repeating direction is the X direction). The bit line 80 is the line and space pattern and, in general, the duty between the line and space is 1:1. The arrangement direction of the gate 65 is the X direction and its repeating direction is the Y direction.

Figure 11:
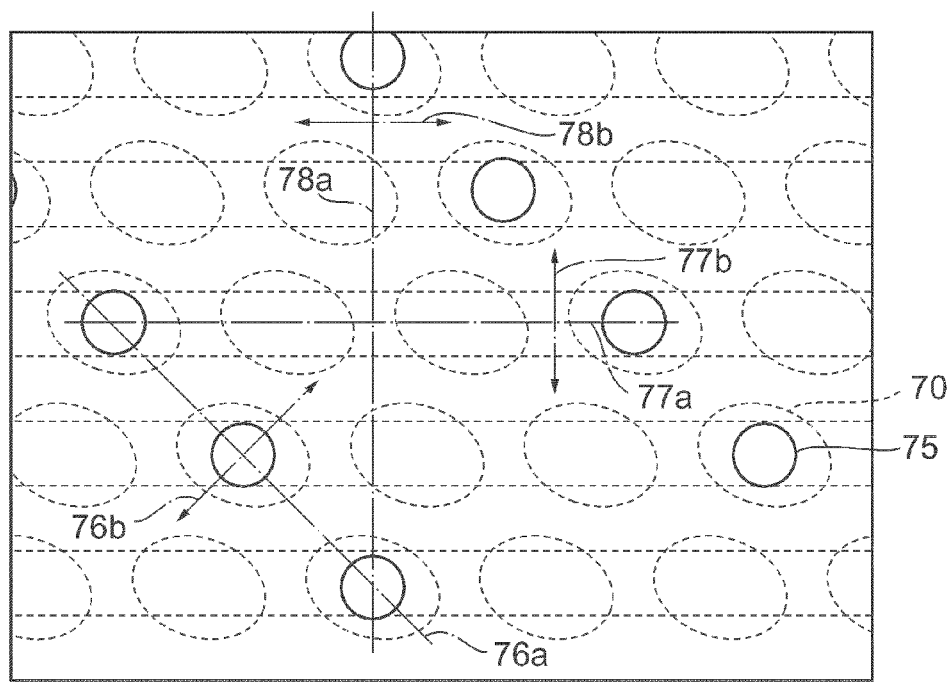
FIG. 11 is a schematic diagram showing a capacitor contact.

The capacitor contact process, as shown in FIGS. 5 and 11, is a critical hole process of forming a capacitor contact 85 to be connected to the cell contact 70 and a cylinder (capacitor) to be described later. In the capacitor contact 85, an arrangement direction 86a in the −45 degree direction, arrangement direction 87a in the zero degree direction (X direction), arrangement direction 88a in the 90 degree direction (Y direction) can be easily found from FIG. 11 and each of the directions perpendicular to these is, respectively, a repeating direction 86b for the arrangement direction 86a in the −45 degree direction, repeating direction 86b for the arrangement direction 87a in the zero degree (X direction), and repeating direction 88b for the arrangement direction 88a in the 90 degree direction (Y direction). Moreover, though there may be other repeating arrangements, details are described by referring to FIG. 23.

Figure 12:
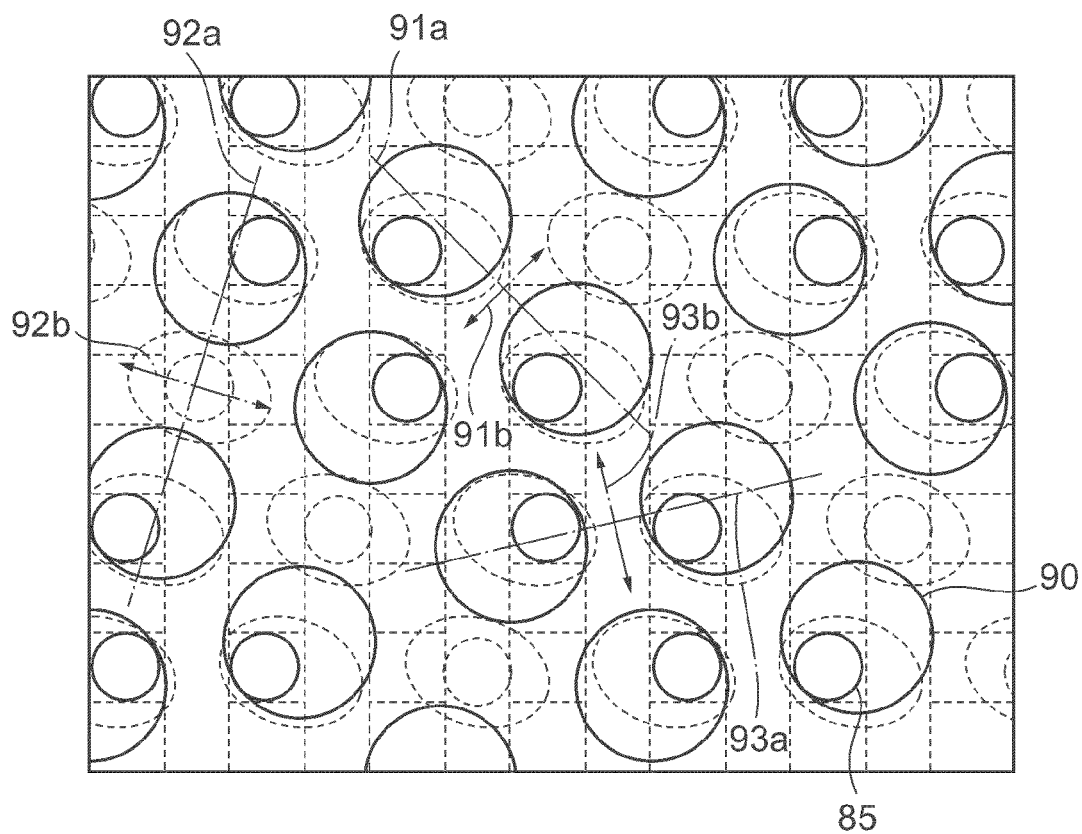
FIG. 12 is a schematic diagram showing a cylinder process.

The cylinder process, as shown in FIGS. 5 and 12, is a critical hole process of forming a cylinder 90 to be connected to the capacitor contact 85. The cylinder 90 has an arrangement direction 91a in the degree direction, arrangement direction 92a in the 72 degree direction, arrangement direction 93a in the 18 degree direction and each of the directions perpendicular to these is, respectively, a repeating direction 91b for the arrangement direction 91a in the −45 degree direction, repeating direction 92b for the arrangement direction 92a in the 72 degree direction, and repeating direction 93b for the arrangement direction 93a in the 18 degree direction. In addition, the cylinder 90 is a capacitor to accumulate electric charges and, therefore, has a comparatively large diameter and a large depth in particular. Furthermore, it is necessary that there is an equal interval among the cylinders 90 being adjacent to one other and that the cylinders are disposed densely and, therefore, the position of the capacitor contact 85 is offset from the position of the cell contact 70 and the positions of the capacitor contacts 85 are offset from one another and, therefore, the cell contact 70 is allowed to have an elliptical shape. After the cylinder process, in general, a wiring process begins.

Figure 13:
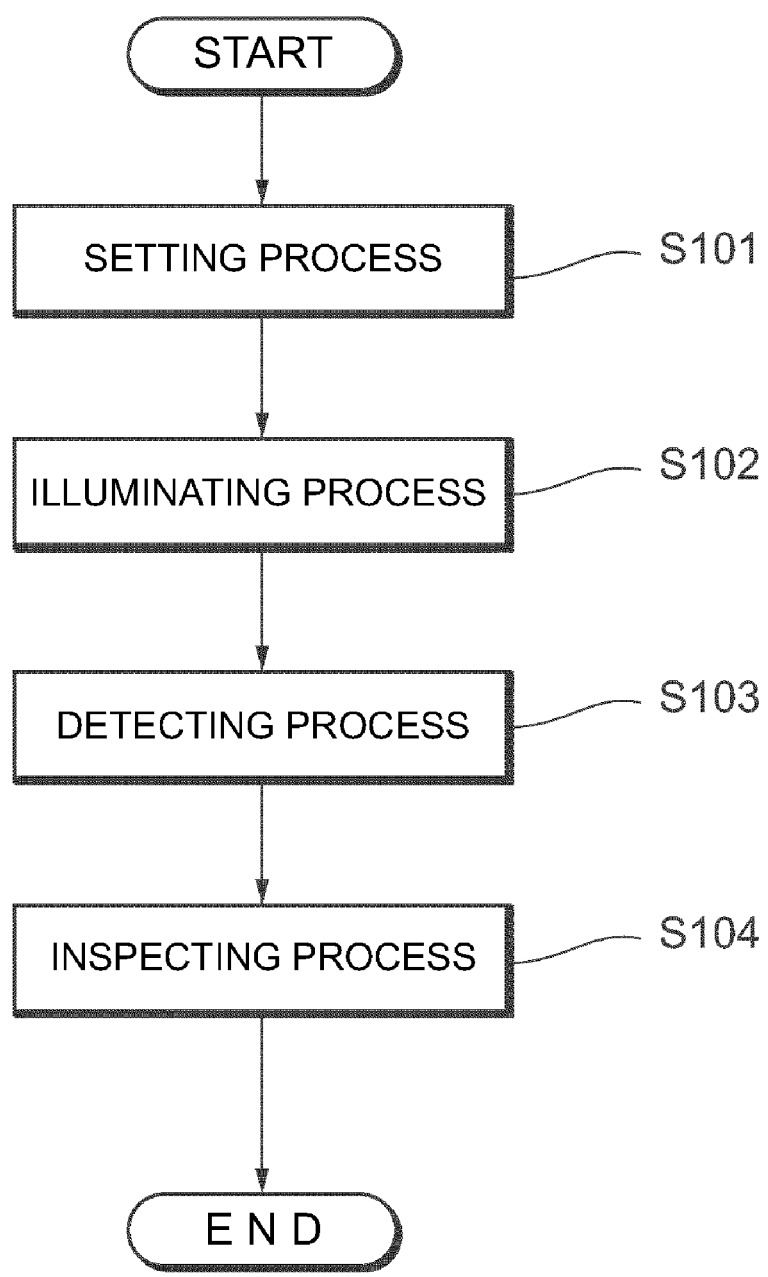
FIG. 13 is a flowchart showing the surface inspection method of the present invention.

The surface inspecting method for semiconductor wafers 50 is described by referring to a flow chart shown in FIG. 13. First, in Step S101, inspecting conditions such as an azimuth angle or tilt angle (illuminating direction of the illumination light 25 on the surface of the wager 50) are set. In the setting process, the inspecting condition setting section 42 makes the θ rotating section 12 and tilting section 13 set an azimuth angle and tilting angle so as to meet the inspecting conditions. Also, the inspecting condition setting section 42 can make the wavelength selecting section 22 select an illuminating wavelength which satisfies the inspecting conditions. Moreover, the inspecting conditions are determined by the FEM evaluating section 43 or the inspecting condition determining section 45 and details are described later.

In a subsequent Step S102, according to the inspecting conditions (azimuth, tilt angle, and the like) set in the Step S101, the surface of the wafer 50 is irradiated with the illumination light 25. In the illuminating process, light emitted from the light source 21 of the illuminating section 20 transmits through the wavelength selecting section 22 and is reflected by the illuminated mirror 23 and becomes the illumination light 25 being collimated flux and is applied to the surface 50. The illumination light 25 becomes light having a wavelength of monochromatic light at the wavelength selecting section 22 and becomes collimated flux at the illuminated mirror 23 and, therefore, parallel rays of the diffracted light 35 are produced from the repeated arrangement pattern of the wafer 50.

In a subsequent Step S103, the diffracted light 35 from the surface of the wafer 50 irradiated with the illumination light 25 is detected. In the detecting process, the rays of the diffracted light 35, after being gathered by the light receiving mirror 31 of the detecting section 30, reach a photographic surface of the photography section 33 through the light receiving lens 32 and forms an image of the wafer 50 on the photographic surface and the image is photographed by the photography section 33. The photography section 33 converts photoelectrically the image on the surface of the wafer 50 formed on the photographic surface into image signals and outputs the image signal to the image processing section 40.

In a subsequent Step S104, based on the diffracted light detected in the Step S103, the existence/nonexistence of defects in a pattern is checked. In the inspection process, the image processing section 40, based on the image signal of the wafer 50 inputted from the photography section 33, compares an inspected image A2 with a non-defective wafer image A1 (see FIG. 3) and also based on results from the comparison (change in an amount of the diffracted light), the inspecting section 41 judges whether there is a defect or not on the wafer 50. As a result, if it is judged by the inspecting section 41 that there is a defect on the surface of the wafer 50, a defect judged image A3 (see FIG. 3) is produced by the image processing section 40 and is then displayed, together with judgment results, in an unillustrated displaying section.

In the conventional inspecting apparatus, when inspecting conditions are to be determined, it is assumed that, as is represented by the line and space pattern, there are many patterns each having repeatability in a 0 degree direction or 90 degree direction and, therefore, the diffraction condition is simply found by using these two azimuths and the diffraction condition is applied also in the hole process. That is, light is applied at the azimuth of 0 degree to check whether the diffracted light can be obtained and the same is then performed at the azimuth of 90 degrees and, if some rays of diffracted light are obtained, the applied condition is registered as an inspecting condition to inspect the semiconductor wafers produced in quantity. Therefore, a case occurs where the inspection is made without knowing from which layer, out of a plurality of layers formed on the surface of a wafer, or without knowing from which arrangement pattern the diffracted light is received. There was, therefore, a fear that the inspection was made in a not-optimized state where diffracted light was received from a lower layer and/or where a change in the CD value could not be detected sensitively.

Additionally, the conventional inspecting technology presents a problem that, due to application of process for higher density to a pattern manufacturing which makes an arrangement pitch smaller, it is made impossible to obtain diffracted light. As the arrangement pitch becomes smaller, diffracted light is produced in an angle direction being far from the angle of the illumination light and, when the angle becomes far relative to the angle of the illumination light, it is practically impossible to receive the diffracted light.

As described above, it seems that an arrangement direction and repeating direction can be found easily from arrangement information of a pattern in the manufacturing process of the wafer 50, however, it is difficult to judge as to which repeating direction of diffracted light can provide the optimum inspecting conditions. This is because the optimum inspecting conditions enabling sensitive defect detection of a change in CD value cannot be determined due to an unknown repeating pitch and due to the occurrence of not only 1st order diffracted light but also 2nd and more higher order diffracted light. Hereinafter, a method for determining inspecting conditions in the setting process of the present embodiment is described in detail.

Figures 14A, 14B, 14C:
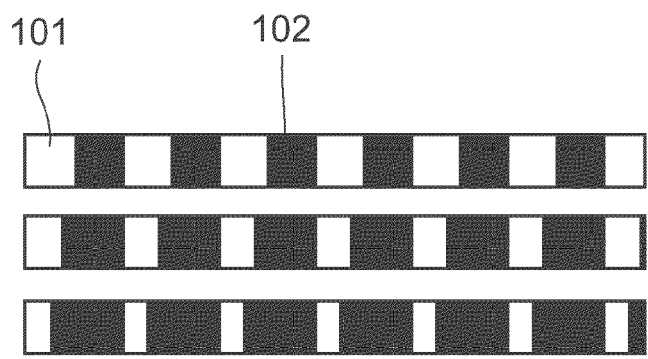
FIGS. 14A, 14B, and 14C are diagrams obtained by modeling a line and space pattern.

First, the case where the CD value is changed in the line and space pattern is explained as the simplest example by referring to FIGS. 14A, 14B, and 14C to 16. FIG. 14A is an explanation model having a pitch with 80 pixels in which the line 101 (white) with 40 pixels and the space 102 (black) with 40 pixels are arranged repeatedly in a horizontally repeating direction. The model shown in FIG. 14A is a model of a non-defective wafer having the duty between the line 100 and space 102 being 1:1 and the information about the arrangement of the model of the non-defective wafer is stored in the arrangement data inputting section 46 (see FIG. 2).

The model shown in FIG. 14B is the model having the line (white) with 30 pixels and space (black) with 50 pixels and the model shown in FIG. 14C is the model having the line (white) with 20 pixels and space (black) with 60 pixels. Therefore, the duty of each of the models shown in FIG. 14A, FIG. 14B, and FIG. 14C is, respectively, 4:4, 3:5, and 2:6. Moreover, the models shown in FIGS. 14B and 14C are set by the CD value change converting section 47. Furthermore, in FIGS. 14A to 14C, no arrangement direction is shown for shorted expression of the models.

Figure 15:
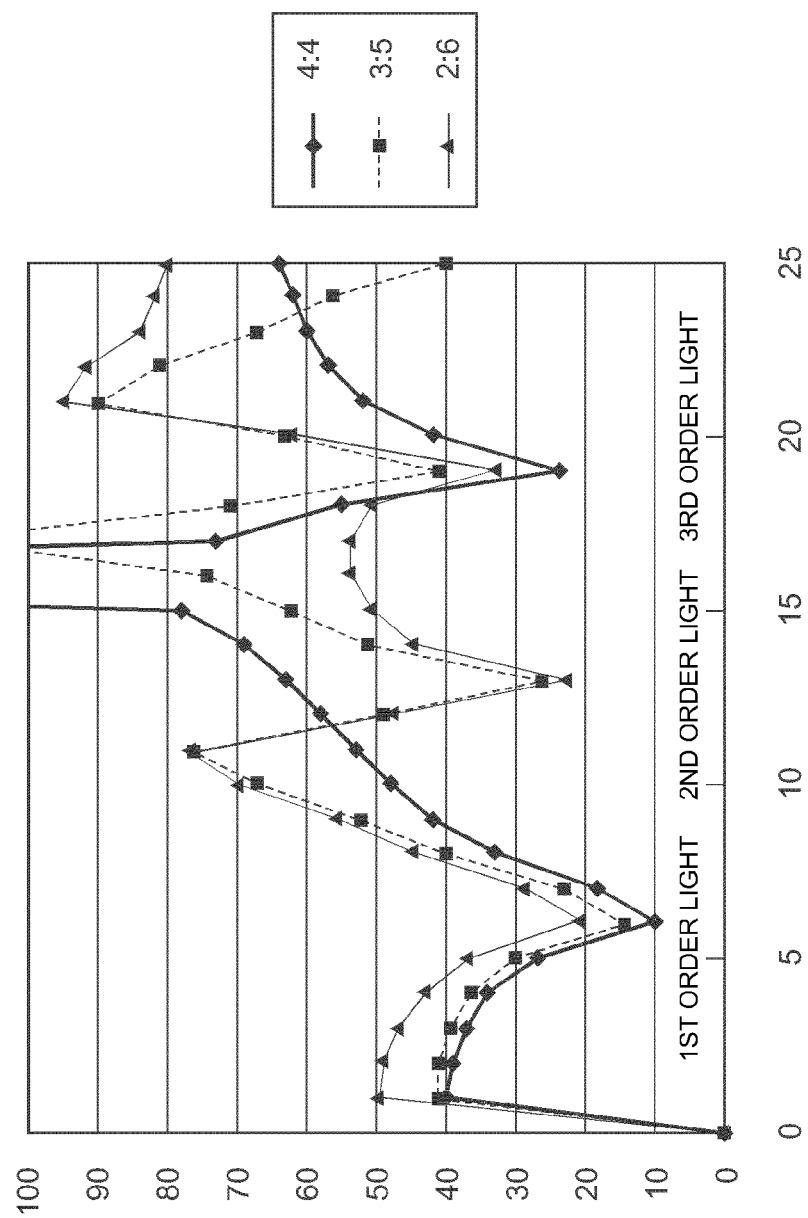
FIG. 15 is a graph showing a relation between a distance from 0th order diffracted light and an amount of diffracted light.

The diffracted light simulator section 48 performs the FFT processing on the models shown in FIGS. 14A to 14C (based on a designed CD value and a changed CD value obtained by the CD value change converting section 47). As the software for the FFT processing, "Scion Image" manufactured by Scion Corp. or "Image Pro" manufactured by Media Cybernetics Co., can be used. FIG. 15 shows changed values after the FFT processing with the repeating direction as an abscissa. The abscissa in FIG. 15 shows a distance from a point of origin (0th order diffracted light) and the larger values represent that the diffracted light is more far from the 0th order diffracted light. The ordinate shows values each corresponding respectively to (not proportional to) an amount of diffracted light and the smaller values represent that the diffracted light is bright.

In FIG. 15, each valley existing near to the values 6, 13, and 19 on the ordinate shows respectively the 1st order diffracted light, 2nd order diffracted light, and 3rd order diffracted light. FIG. 15 shows that, in the line and space pattern (model of non-defective wafer) having the duty of 1:1 (in the case where the duty is 4:4 in the present calculation), the 2nd order diffracted light is not produced optically and theoretically, however, as is apparent from FIG. 15, in the case of the curve having the duty of 4:4, no valley exists near to the value 13 on the abscissa and the 2nd diffracted light is not produced. Also, the 3rd diffracted light occurs for every duty, however, an amount of diffracted light is smaller than that of the 1st diffracted light. However, if the amount of the 3rd diffracted light is decreased to about one tenth or one hundredth level compared with the 1st diffracted light, it presents a problem from the viewpoint of detection accuracy. However, the ratio of the amount of the 3rd diffracted light shown in FIG. 15 to the amount of the 1st diffracted light is not large enough to produce any problem.

Now, the detection sensitivity to the CD value change, which is most important, is evaluated. This evaluation is performed by the CD value change converting section 47 and diffracted light simulator section 48. The CD value change is a phenomenon that occurs in so-called defocus defects in many cases and, in the semiconductor manufacturing process, irrespective of the cause for the occurrence, the CD value is the value to be severely controlled. In order to evaluate the detection sensitivity to the CD value change, as shown in FIG. 16, the change in an amount of the 1st and 2nd order diffracted light corresponding to a change in the duty is first to be observed. In FIG. 16, the duty (4:4 for non-defective wafer, 3:5, and 2:6) is plotted as abscissa and a ratio (relative value) of each amount of diffracted light to the amount of diffracted light obtained when the duty is 4:4 as ordinate. In the case of the 1st order diffracted light, when the duty is 4:4, 3:5, and 2:6 in FIG. 15, the values on the ordinate are 10, 14, and 21 respectively and, therefore, in FIG. 16, when the duty is 3:5 and 2:6, absolute values are 14/10=1.4 and 21/10=2.1, respectively. The same calculation can be also applied to the 3rd order diffracted light.

As is understood from FIG. 16, the amount of the 1st order diffracted light changes almost linearly in response to the change in the CD value of a line width. On the other hand, the amount of the 3rd order diffracted light changes non-linearly, however, the change in the amount of diffracted light is large when the duty is 3:5 and, therefore, so long as this point is concerned, the 3rd order diffracted light is more sensitive compared with the 1st order diffracted light. However, the diffraction angle (angle formed by incident light and diffracted light) of the 3rd diffraction angle is larger by about 3 times than that of the 1st diffracted light. In the DRAM of 2F=about 0.14 μm which is called a "70 nm generation DRAM", when practical light source wavelength and optical placement are considered, if the pitch is 0.14 μm, the 3rd diffracted light cannot be received. Therefore, in this case, the inspecting condition is determined by the diffracted light simulator section 48 so that the 1st diffracted light which is practically optimum light can be received and the determined inspecting condition data is outputted from the inspecting condition data outputting section 49 to the inspecting condition determining section 42. Then, the inspecting condition determining section 42 tilts the stage 11 (wafer 50) so that the receipt of the 1st order diffracted light as the inspecting condition determined by the inspecting condition determining section 45 can be realized.

Thus, it has been found by calculation evaluation of sensitivity to the change in amounts of diffracted light corresponding to the CD value change that there is the case in which higher order diffracted light (3rd diffracted light in the case shown in FIG. 16) can more sensitively detect the CD value change compared with the 1st diffracted light and this fact can be effectively used as a judgment standard for determining the optimum inspecting condition. Details are described later.

Now, another method for determining inspecting conditions sensitive to the CD value change, that is, the FEM evaluation to be performed by the FEM evaluating section 43 is described by referring to FIGS. 17 to 19A and 19B. The FEM evaluating section 43 determines inspecting conditions by using a wafer prepared for evaluation.

The wafer for evaluation, as shown in FIG. 17, is called an "FEM wafer 110" on which exposure conditions are changed stepwisely for every row and every column of the exposure shot 111. More specifically, in the shots (rows) arranged in up and down directions, exposure is performed by changing a dose amount (exposure energy) and, in the shots (columns) arranged in left and right directions, exposure is performed by changing an amount of focus offset. The CD value of the FEM wafer 110 is measured for every exposure shot, which is used for evaluating optimum exposure conditions for a semiconductor wafer and optimum process margin (process window). For example, in the case of an ArF exposing machine, an optimum dose condition is determined by the CD value obtained based on the measurement using the SEM or the like, however, in the case where the dose amount is 40 mJ/cm², exposure is performed by setting the dose amount to be 35 mJ/cm² for the shot located on the uppermost row and the exposure is continued by decreasing the dose amount by 1 mJ/cm² for every lower row. As a result, the dose amount becomes 35, 36, 37, . . . , 45 mJ/cm² in each shot and, on the row 112 being a central shot, the dose amount becomes 40 mJ/cm² being the optimum dose amount. On the other hand, as a result from the measurement of CD values by the SEM or the like, if the optimum focus condition (focus margin) is −0.2 μm to +0.15 μm, the exposure is performed by setting the focus step to be 0.05 μm and adding the focus step of −0.3, −0.25, . . . , +0.20 μm to every column on the right side sequentially from the shot located on a left-end column.

In order to determine inspecting conditions by using the FEM wafer 110 as described above, the surface of the FEM wafer 110 is irradiated with the illumination light 25 by using the illuminating section 20 shown in FIG. 1 and the diffracted light 35 is detected from the FEM wafer 110 by using the detecting section 30 to obtain an inspected image of the FEM wafer 110. For example, when the FEM wafer 110 is used for inspecting the bit contact 75 shown in FIG. 9, the arrangement direction is −45 degree direction or 0 degree direction (or 90 degree direction). Moreover, the bit contact 75 is connected to the bit line 80 and, therefore, the arrangement pitch can be handled as being already known based on the arrangement pitch of the bit line. Based on the arrangement information described above, inspecting conditions are set by the inspecting condition setting section 42 to obtain the inspected image of the FEM wafer 110.

The inspected image (image signal) of the FEM wafer 110 is inputted from the image processing section 40 to the FEM evaluating section 43 where an average luminance within a shot is calculated for every exposure shot 111. It is assumed, for example, that an illumination map shown in FIG. 18A under the condition for obtaining diffracted light from 0 degree direction 77a is obtained and that an illumination map shown in FIG. 19A under the condition for obtaining diffracted light from −45 degree direction 76a (see FIG. 9) is obtained (light and shade of the exposure shot 111 in each drawing represents the degree of luminance). At this point of time, a shot receiving the optimum dose amount (40 mJ/cm²) is the row 112 of the central shot and the graphs in FIGS. 18B and 19B can be obtained by calculating average luminance at each shot in the row 112 of the central shot for graphing curved-line approximation. Values obtained by swinging the focus in the row 112 in the central shot (shot receiving the optimum dose amount) are plotted as abscissa shown in FIGS. 18B and 19B. Namely, the values correspond to the focus off-set of "−0.3, −0.25, . . . +0.20 μm". The average luminance in each shot is plotted as ordinate.

As is apparent from FIGS. 18B and 19B, the CD value change produced by the focus offset is more sensitively detected as the change in the amount of diffracted light in the luminance change (FIG. 19B) occurred when conditions for obtaining diffracted light from −45 degree arrangement direction 76a are used as the inspecting condition, in spite of the same wafer, rather than in the luminance change (FIG. 18B) occurred when conditions for obtaining diffracted light from the 0 degree arrangement direction 77a are used as the inspecting conditions.

Then, such judgment is automatically made (through numerical calculation or the like) by the FEM evaluating section 43 and the condition for obtaining diffracted light form the −45 degree arrangement direction 76a is determined as the inspecting condition and the determined inspecting condition data is outputted to the inspecting condition setting section 42.

Figure 20:
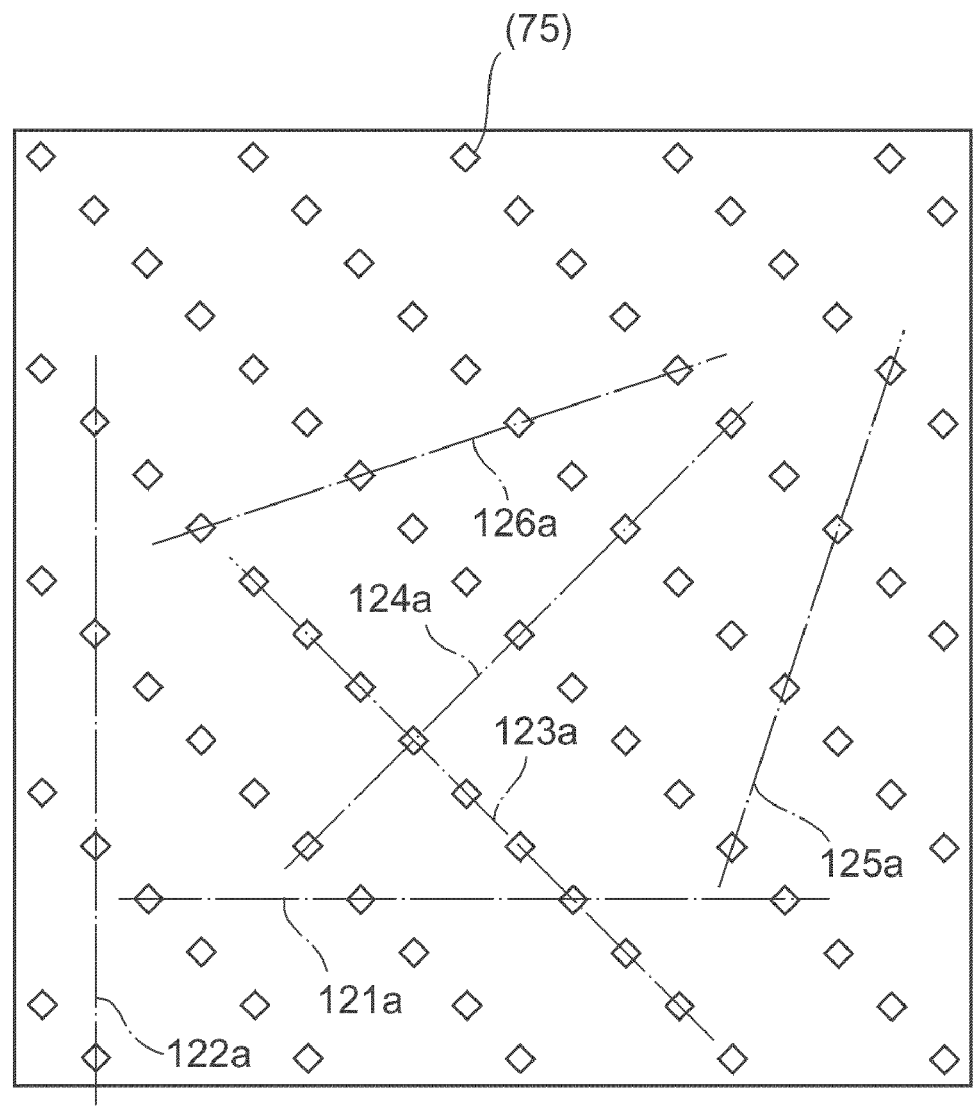
FIG. 20 is a diagram showing a result from an FFT (Fast Fourier Transform) processing performed on a bit contact model.

The method is described for determining inspecting conditions according to the evaluation of the arrangement direction (or repeating direction) performed by the FEM evaluating section 43 and inspecting condition determining section 45 from the arrangement information about repeating arrangement pattern. FIG. 20 is a modeled diagram of the bit contact 75 shown in FIG. 9 and it is assumed that the arrangement information about the bit contact 75 is stored in the arrangement data inputting section 46. As shown in FIG. 20, the bit contact 75 has the arrangement direction 121a in the 0 degree direction, arrangement direction 122a in the 90 degree direction, arrangement direction 123a in the −45 degree direction, arrangement direction 124a in the 45 degree direction, arrangement direction 125a in the 72 degree direction, and arrangement direction 126a in the 18 degree direction.

Figure 21:
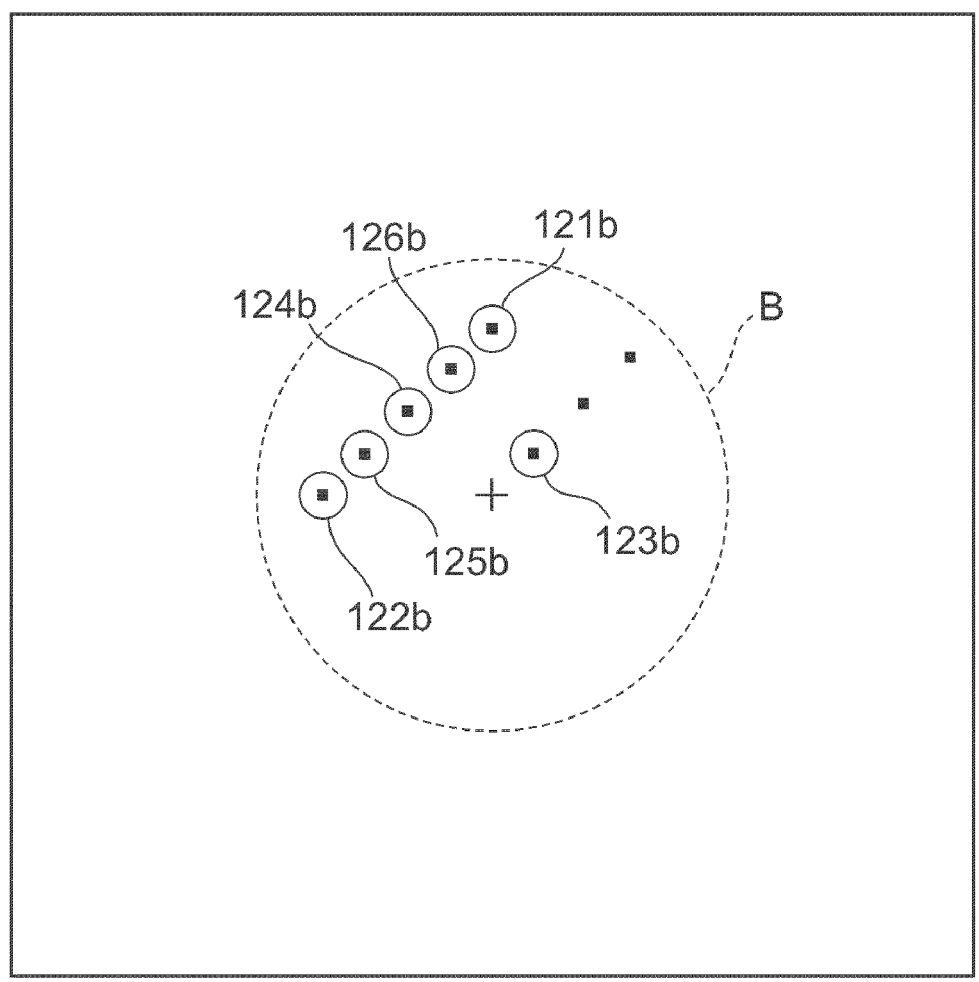
FIG. 21 is a diagram showing a result from FFT processing performed on a bit contact model.

FIG. 21 shows a diagram obtained by performing FTF processing on the model in FIG. 20 by using the diffracted light simulator section 48 and by displaying a region near to a point of origin in an enlarged manner. In FIG. 21, rays of diffracted light 121b to 126b are shown each corresponding respectively to the arrangement direction 121a in the 0 degree direction, arrangement direction 122a in the 90 degree direction, arrangement direction 123a in the −45 degree direction, arrangement direction 124a in the 45 degree direction, arrangement direction 125a in the 72 degree direction, and arrangement direction 126a in the 18 degree direction. The center of FIG. 21 is a point of origin and, when light having a specific wavelength enters, from a direction perpendicular to the paper surface, the repeating arrangement pattern as shown in FIG. 20, the diffracted light pattern passing through the pupil surface on a reflecting surface side or transmitting surface side can be FIG. 21. Therefore, the center of FIG. 21 (point of origin) corresponds to 0th order diffracted light (regularly reflected light). The direction directing toward the rays of diffracted light 121b to 126b from the center of FIG. 21 is a repeating direction (as described above, the repeating direction is perpendicular to an arrangement direction). Moreover, the distance from the center of FIG. 21 (point of origin) to the rays of diffracted light 121b to 126b corresponds to a diffraction angle.

The diffracted light receivable range B in which diffracted light can be received is shown in FIG. 21 and the range B is obtained by using the 70 nm generation DRAM having 2F being 0.14 μm and by considering actually adapted configurations (for example, to what degree the light having a short wavelength can be used as incident light or to what degree the tilting section can make an incident angle larger accurately) for the surface inspecting apparatus 1. For example, diffracted light 123b corresponding to the arrangement direction 123a in the −45 degree direction occurs at a position near the point of origin (small diffraction angle) and, in order to receive the diffracted light 123b, the wafer 50 is simply rotated toward the direction in which diffracted light is produced by 45 degrees using the θ rotating section 12 and is simply tilted to have a tilt angle corresponding to a diffraction angle using the tilting section 13. Also, for example, the diffracted light 121b corresponding to the arrangement direction 121a in the 0 degree direction occurs at a position being far from the point of origin (that is, diffraction angle is large), however, the position is within the diffracted light receiving range B and, therefore, the diffracted light can be received. In order to receive the diffracted light 121b, the rotation of the wafer 50 using the θ rotating section 12 is not required (in the same state in FIG. 4A) and setting of the tilt angle is enough, however, due to the large tilt angle, considerable tilting of the wafer 50 is required.

Figures 22A, 22B, 22C, 22D:
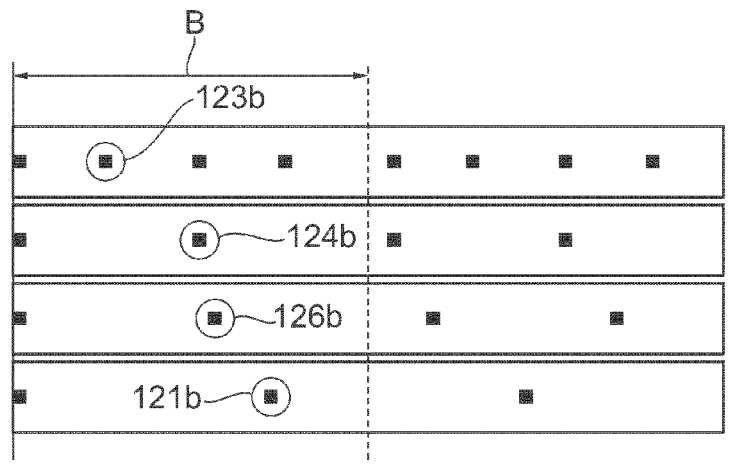
FIG. 22A to 22D are diagrams showing diffraction light distribution in a moving radius direction in FIG. 21.

FIGS. 22A, 22B, 22C, and 22D show diffracted light distribution in moving directions in FIG. 21 each corresponding respectively to the azimuth angle at which each of rays of diffracted light corresponding to the arrangement direction 123a in the −45 degree direction, arrangement direction 124a in the 45 degree direction, arrangement direction 126a in the 18 degree direction, and arrangement direction 121a in the 0 degree direction is received. Moreover, the left end point in each of FIGS. 22A to 22D is a point of origin (0th order diffracted light) and the range from the left end to a broken line is the diffracted light receiving range B. For example, as shown in FIG. 22A, it is understood that, at the azimuth angle at which the diffracted light 123b corresponding to the arrangement direction 123a in the −45 degree direction is received, a plurality of rays of diffracted light, excepts the diffracted light 123b surrounded by a circle, is produced depending on the diffraction angle (corresponding to a horizontal direction). That is, it is also understood that, when the arrangement model of the bit contact 75 shown in FIG. 20 is evaluated by making the diffracted light simulator section 48 perform the FFT processing, actually, various rays of diffracted light are produced in various repeating directions. This is because high order diffracted light having a specified repeating pitch is contained. These rays of diffracted light appear also in FIG. 21, however, for easy explanation, their illustrations are omitted.

The inspecting condition determining section 45 inputs conditions (azimuth and tilting angle) for obtaining diffracted light from the arrangement direction 123a in the −45 degree direction, as inspecting conditions, into the inspecting condition setting section 42, which then rotates the wafer 50 using the θ rotating section 12 toward the direction in which the diffracted light from the arrangement direction in the −45 degree direction can be received and continuously changes (tilts the wafer continuously) the tilt angle within the diffracted light receivable range B using the tilting section 13 so that some rays of diffracted light can be received at a specified azimuth. The image of the FEM wafer 110 obtained at a plurality of tilt angles enabling the receipt of diffracted light is obtained using the FEM wafer 110 described above and the FEM evaluating section 43, using the same method employed in FIGS. 17 to 19, evaluates a tilt angle being sensitive to the CD value change and determines inspecting conditions (tilt angle) for inspecting the wafer 50 to be inspected. The FEM evaluating section 43 outputs the determined inspecting condition to the inspecting condition setting section 42, which operates the θ rotating section 12 and tilting section 13 so that the determined inspecting conditions (azimuth and tilt angle) are set.

Furthermore, when the image of the FEM wafer 110 at a plurality of tilt angles is to be obtained, images are acquired for every different wavelength by the wavelength selecting section 22 and the wavelength and tilt angle being sensitive to the CD value change may be evaluated by the FEM evaluating section 43 to determine inspecting conditions (wavelength and tilt angle) for inspecting the wafer 50.

After determining the arrangement direction (arrangement direction 123a or the −45 degree direction in the bit contact 75) in which diffracted light is obtained, without using the FEM wafer 110 and FEM evaluating section 43, by using the same method employed in FIGS. 14A, 14B, and 14C to 16, the CD value change may be set by the CD value change converting section 47 and the FFT processing is performed by the diffracted light simulator section 48 on a design CD value (non-defective model) and change CD value to obtain diffracted light being sensitive to the CD value change and to determine inspecting conditions for receiving the diffracted light.

Thus, according to the present embodiment, the simulation of a change in amounts of diffracted light is performed in a manner to match a change (change in CD values) in shape of a hole pattern (such as bit contact 75 or the like) and, therefore, the optimum inspecting conditions can be determined according to quantitative judgment criteria. In the case of DRAM in particular, there are many arrangement directions compared with flash memories or the like, the present invention is effective. Furthermore, the inspecting conditions can be determined from the viewpoint of sensitivity to the CD value change, thus enabling matching with the CD values in the semiconductor manufacturing processes to be easily achieved.

Figure 23:
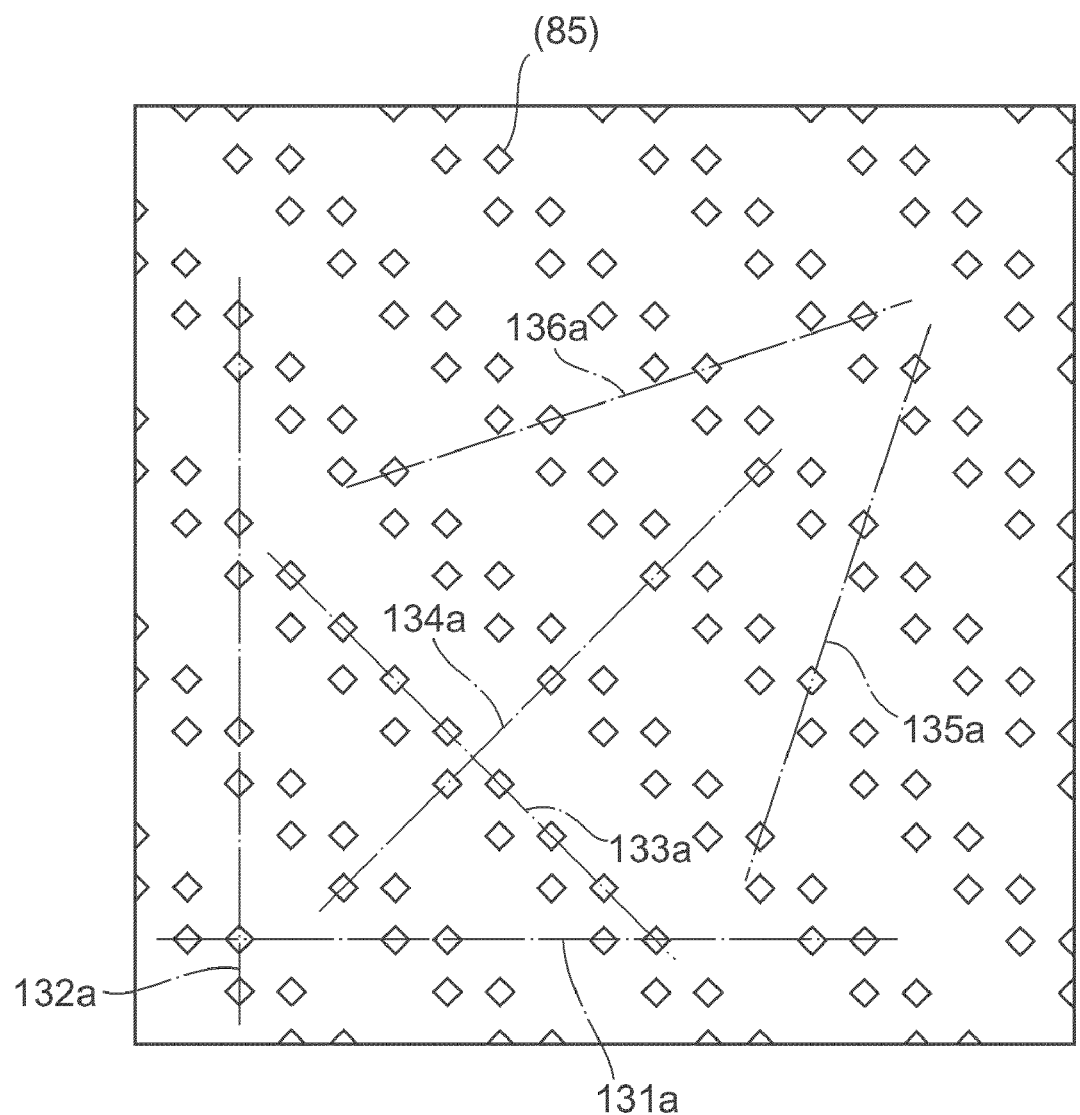
FIG. 23 is a diagram obtained by modeling a capacitor contact process.

Moreover, the present invention is effective in the inspection of not only bit contacts but also cell contacts 70, capacitor contacts 85, and cylinders 90 and also in the inspection of field processes. FIG. 23 is a diagram obtained by modeling the capacitor contacts 85 shown in FIG. 11 and shows that the inspecting conditions can be determined by the same method employed in the above embodiment. FIG. 23 shows that the capacitor contacts 85 have the arrangement direction 131a in the 0 degree direction, arrangement direction 132a in the 90 degree direction, arrangement direction 133a in the −45 degree direction, arrangement direction 134a in the 45 degree direction, arrangement direction 135a in the 72 degree direction, and arrangement direction 136a in the 18 degree direction.

Figure 24:
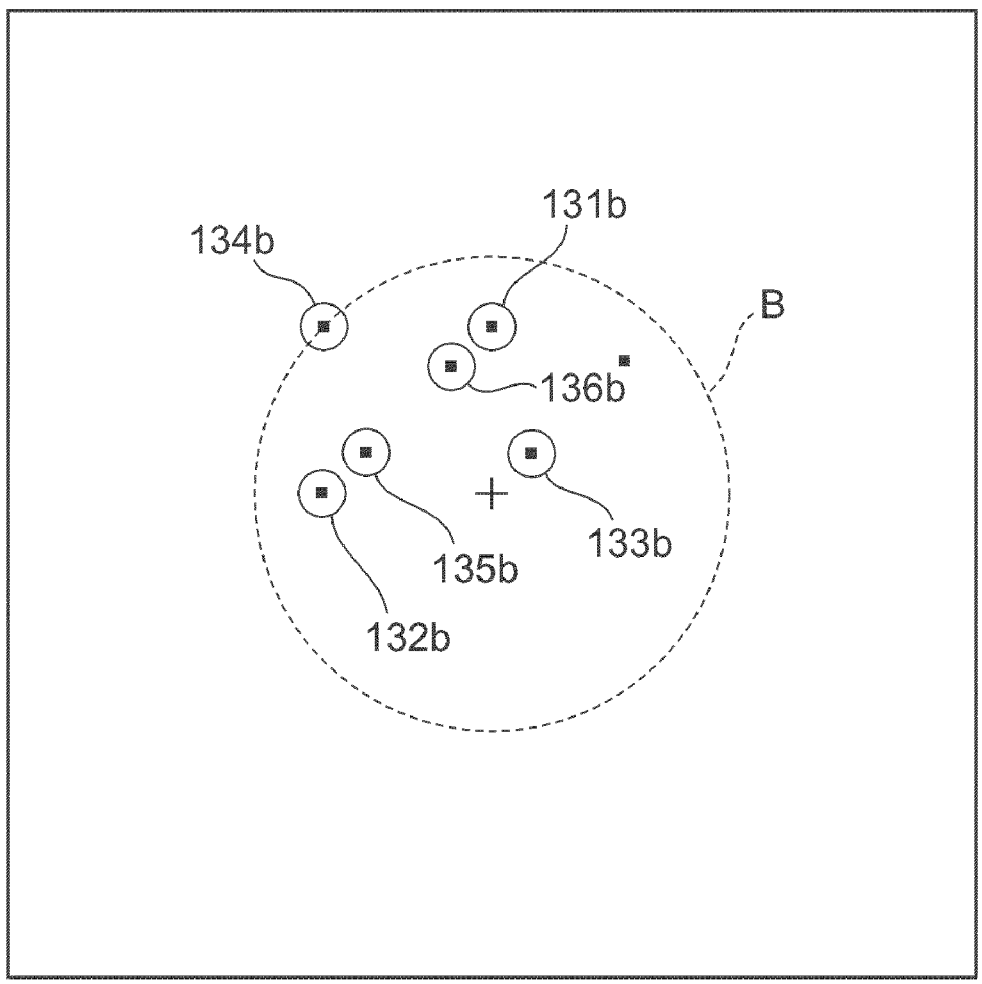
FIG. 24 a diagram showing a result from FFT processing performed on a capacitor contact model.

FIG. 24 is a diagram obtained by performing FFT processing on the model in FIG. 23 using the diffracted light simulator section 48 and by displaying a region near to its point of origin in an enlarged manner. In FIG. 24, rays of diffracted light 131b to 136b are shown each corresponding respectively to the arrangement direction 131a in the 0 degree direction, arrangement direction 131a in the 90 degree direction, arrangement direction 133a in the −45 degree direction, arrangement direction 134a in the 45 degree direction, arrangement direction 135a in the 72 degree direction, and arrangement direction 136a in the 18 degree direction. As is apparent from FIG. 24, the diffracted light 134b corresponding to the arrangement direction in the 45 degree direction cannot be received since the diffracted light occurs out of the diffracted light receiving range B.

Figures 25A, 25B, 25C:
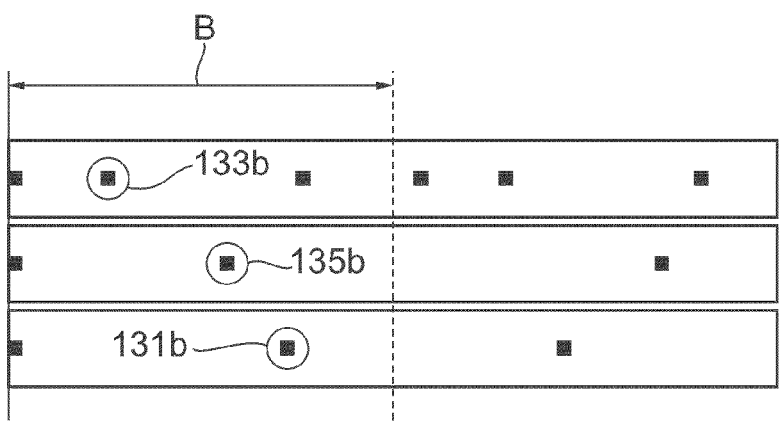
FIGS. 25A, 25B, and 25C are diagrams showing diffracted light distribution in a moving radius direction in FIG. 24.

FIGS. 25A, 25B and 25C show diffracted light distribution in moving radius directions in FIG. 24, each corresponding respectively to the azimuth angle at which each of rays of diffracted light corresponding to the arrangement direction 133a in the −45 degree direction, arrangement direction 135a in the 72 degree direction, and arrangement direction 131a in the 0 degree direction is received. As is understood from FIG. 25A, at the azimuth angle at which the diffracted light 133b corresponding to the arrangement direction 133a in the −45 degree direction, a plurality of diffracted light is produced according to a diffraction angle (corresponding to a horizontal direction) excepts the diffracted light 133b surrounded by a circle.

Figure 26:
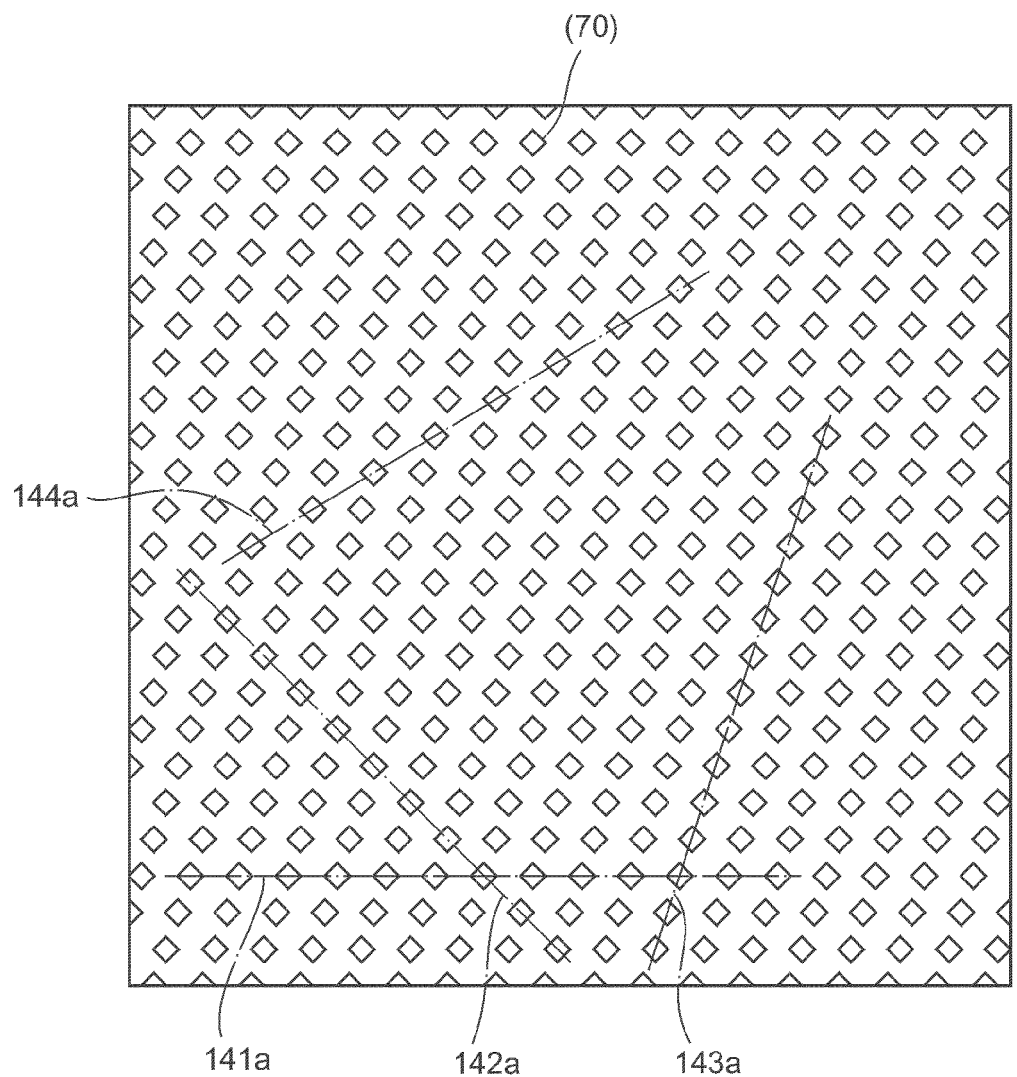
FIG. 26 is a diagram obtained by modeling a cell contact process.

FIG. 26 is a diagram obtained by modeling the cell contact 70 shown in FIG. 8 and inspecting conditions can be determined using the process employed in the above embodiment. As shown in FIG. 26, the cell contact 70 has an arrangement direction 141a in the 0 degree direction, arrangement direction 142a in the −45 degree direction, arrangement direction 143a in the 72 degree direction, and arrangement direction 144a in the 31 degree direction.

Figure 27:
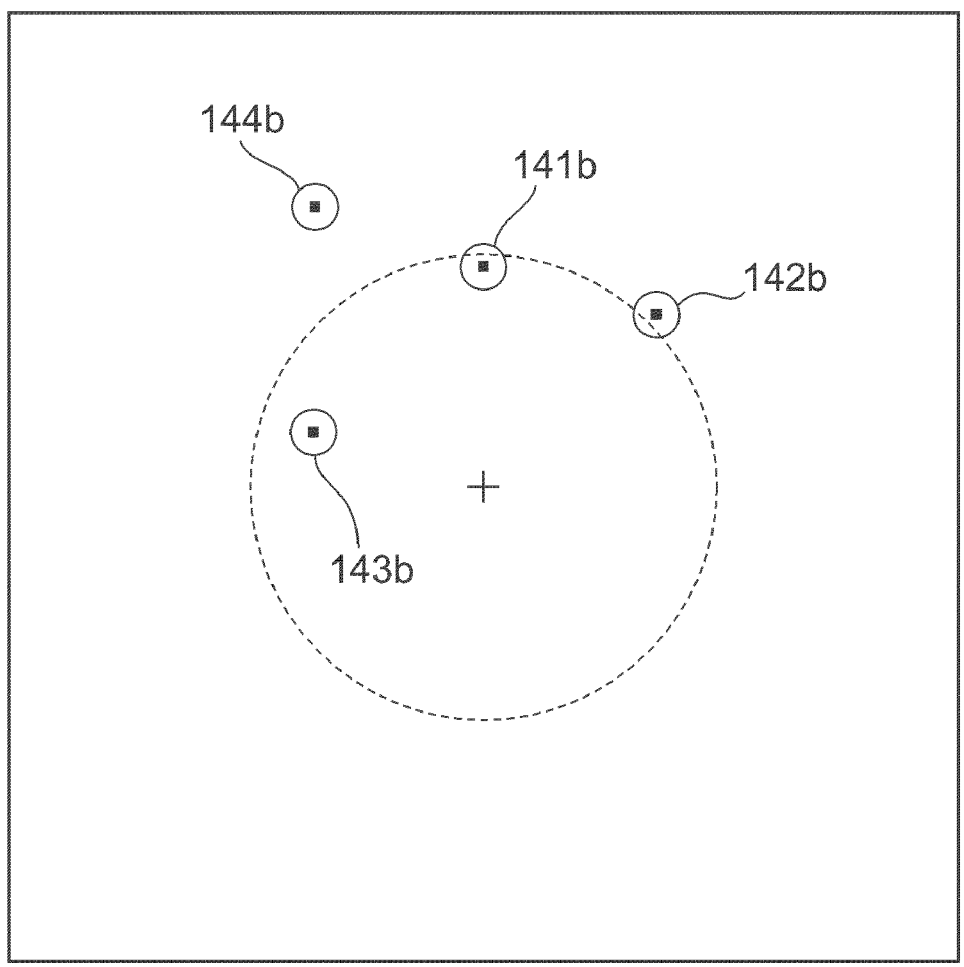
FIG. 27 a diagram showing a result from FFT processing performed on a cell contact model.
Figures 28A, 28B, 28C, 28D:
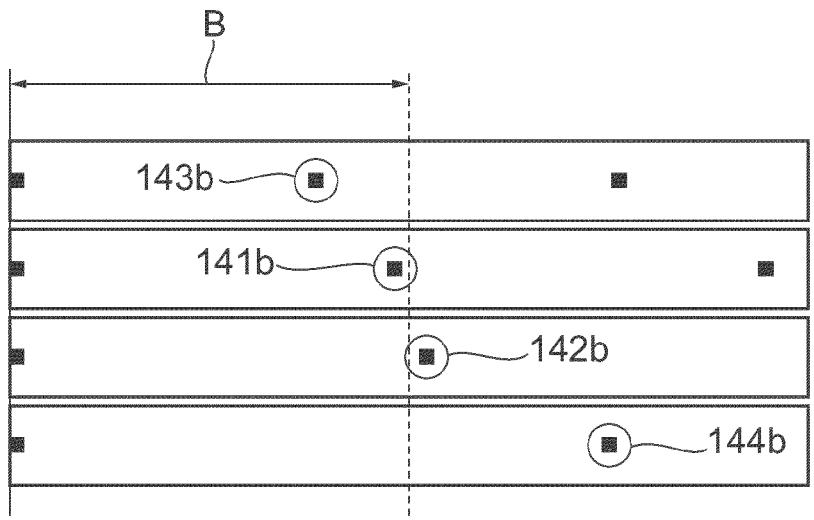
FIGS. 28A, 28B, 28C, and 28D are diagrams showing diffracted light distribution in a moving radius direction in FIG. 27.

FIG. 27 is a diagram obtained by performing FFT processing on the model in FIG. 26 using the diffracted light simulator section 48 and by displaying a region near to its point of origin in an enlarged manner. In FIG. 27, rays of diffracted light 141b to 144b are shown each corresponding respectively to the arrangement direction 141a in the 0 degree direction, arrangement direction 142a in the −45 degree direction, arrangement direction 143a in the 72 degree direction, and arrangement direction 144a in the 31 degree direction. As is apparent from FIG. 27, the diffracted light 142b corresponding to the arrangement direction 142a in the −45 degree direction and diffracted light 144b corresponding to the arrangement direction 144a in the 31 degree direction cannot be received since these rays of diffracted light occur out of the diffracted light receiving range B. The rays of diffracted light 141b and 143b each corresponding respectively to the arrangement direction 141a in the 0 degree direction and the arrangement direction 143a in the 72 degree direction can be received.

FIGS. 28A, 28B, 28C, and 28D show diffracted light distribution in moving radius directions each corresponding respectively to the azimuth angle at which each of rays of diffracted light corresponding to the arrangement direction 143a in the 72 degree direction, arrangement direction 141a in the 0 degree direction, arrangement direction 142a in the −45 degree direction, arrangement direction 144a in the 31 degree direction is received. As is apparent from FIGS. 28A to 28D, no diffracted light occurs (within the diffracted light receiving range B) other than the diffracted light surrounded by a circle. That is, it is understood that, in the cell contact 70, only the arrangement direction 141a in the 0 degree direction and arrangement direction 143a in the 72 degree direction can be set as the inspecting conditions.

As described above, in the conventional inspecting apparatus, only the arrangement direction in the 0 degree direction and arrangement direction in the 90 degree direction can be set. This is because arrangement information has not been used for condition setting in the conventional apparatus. As a result, in the cell contact 70, the inspecting condition for receiving only diffracted light from the arrangement direction in the 0 degree direction has been set. However, in the case of DRAM manufactured by a process for higher device density, when the cell contact is proportionally contracted, the inspection is impossible according to the inspecting conditions set only for the arrangement direction in the 0 degree direction.

Figure 29:
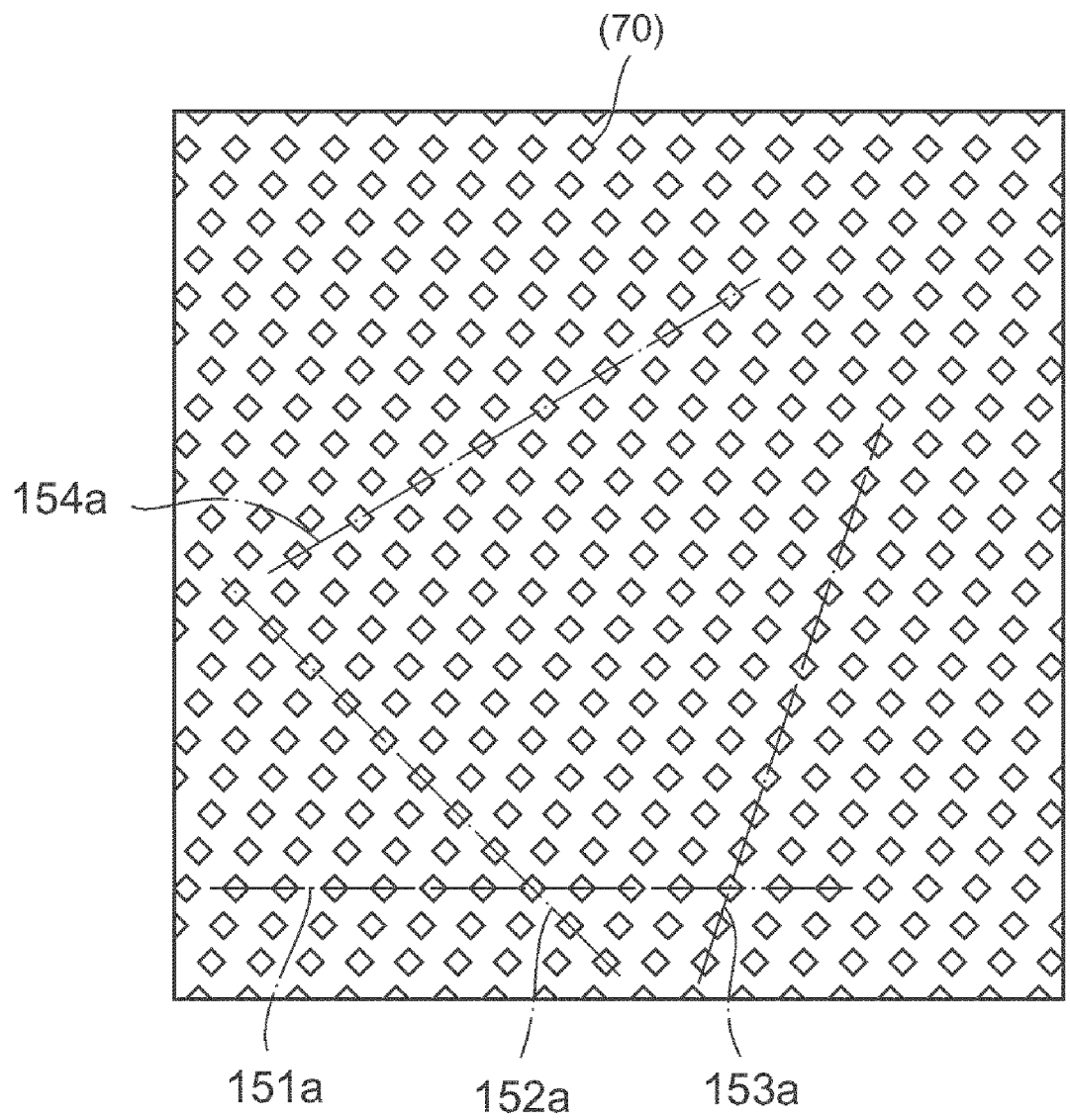
FIG. 29 is a diagram showing a model obtained by contracting by 20% the cell contact in FIG. 26.
Figure 30:
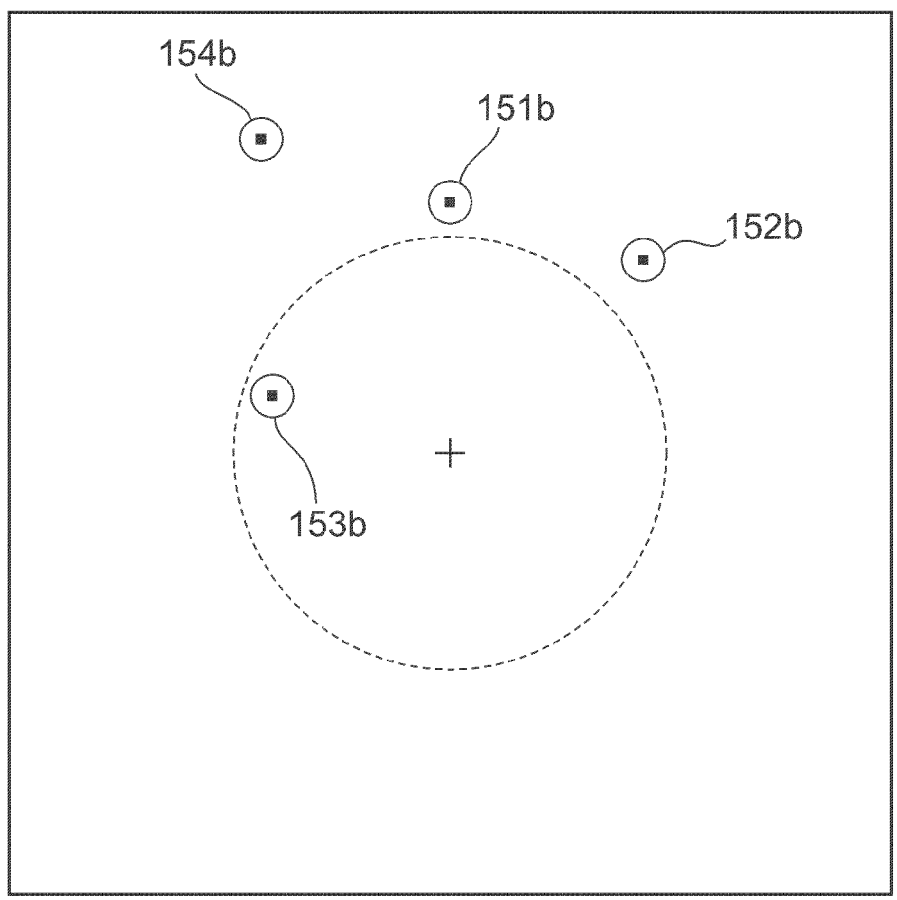
FIG. 30 is a diagram showing a result from FFT processing performed on the model in FIG. 29.
Figure 31:
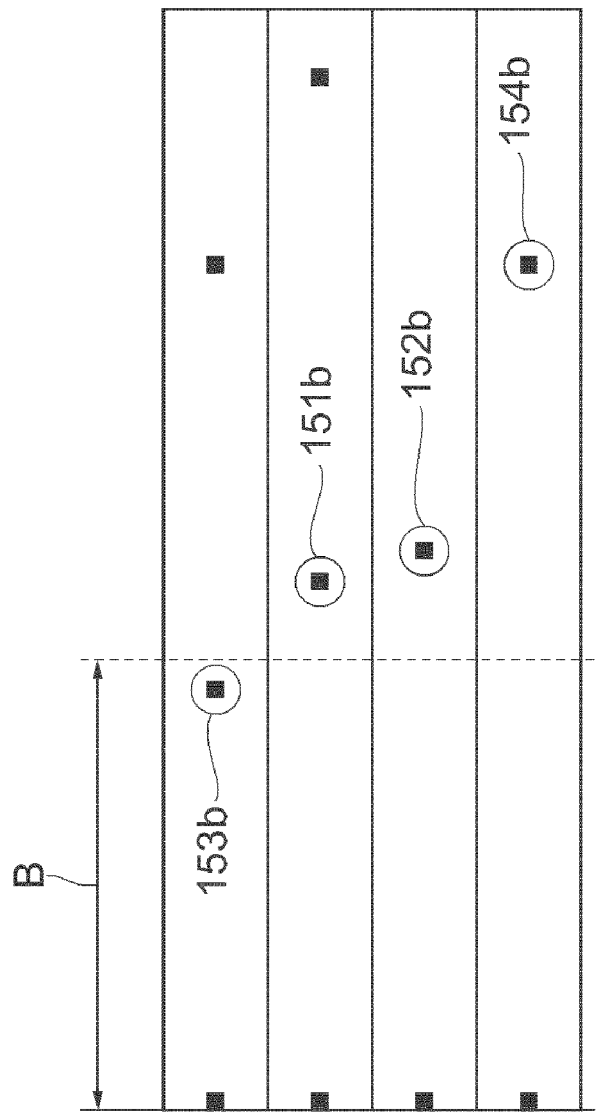
FIGS. 31A, 31B, 31C, and 31D are diagrams showing diffracted light distribution in a moving radius direction in FIG. 30.

FIG. 29 is a diagram showing a model obtained by contracting the cell contact 70 by about 20% and FIG. 30 is a diagram obtained by performing FFT processing using the diffracted light simulator section 48 and by displaying a region near to a point of origin in an enlarged manner. As is apparent from FIG. 30, out of rays of diffracted light 151b to 154b each corresponding respectively to the arrangement direction 151a in the 0 degree direction, arrangement direction 152a in the −45 degree direction, arrangement direction 153a in the 72 degree direction, arrangement direction 154a in the 31 direction, only the diffracted light 153b corresponding to the arrangement direction 153a in the 72 degree direction can be received. This is also apparent from the diffracted light distribution in the moving radius direction in FIG. 30 shown in FIGS. 31A to 31D.

Figure 32:
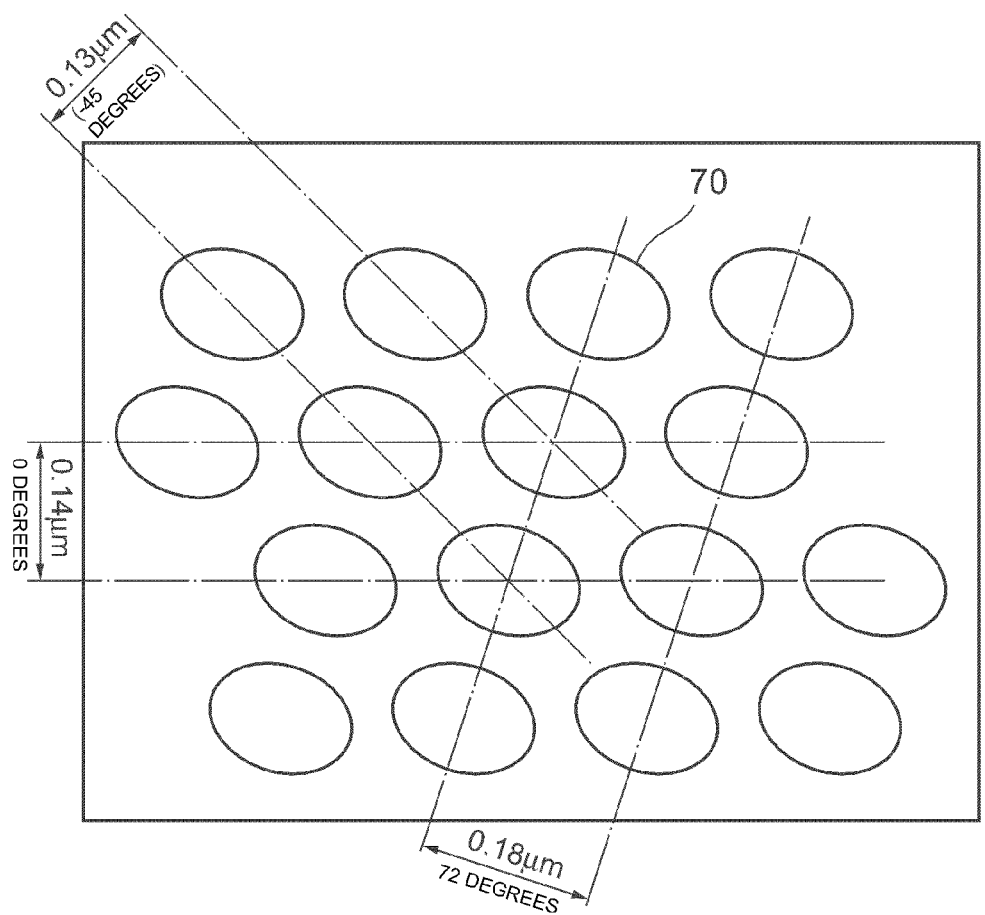
FIG. 32 is a diagram showing an arrangement direction and a pitch of the cell contact.

FIG. 32 is a diagram showing an arrangement direction and repeating pitch to be applied to the cell contact shown in FIG. 8. Here, 2F=0.14 μm. FIG. 32 shows that, in the arrangement direction in 72 degree direction, the repeating pitch is about 0.18 μm which is large compared with other arrangement directions. Therefore, even if the repeating pitch is contracted by about 20%, the repeating pitch becomes 0.144 [(0.18×0.8)=0.144] μm and is still within the diffracted light receiving range. That is, in the cell contact 70, the arrangement direction allowing the repeating interval of holes adjacent to one another to be largest is preferably set as the inspecting conditions.

It has been already described that the cell contact 70 is elliptical and its short diameter director is the arrangement direction 72a in the 72 degree direction (see FIG. 8). On the other hand, in the model of the cell contact 70 as shown in FIGS. 26 and 29, its elliptical shape and its duty (the size of the ellipse, ratio regarding an interval between ellipses adjacent to one another), direction of the ellipse, that is a relation between short diameter direction and arrangement are not taken into consideration. By using the shape information being near to an actual state as arrangement information and by evaluating the diffracted light using the diffracted light simulator section 48, in some cases, 1st order diffracted light and higher order are produced from the repeating pitch having a longer period. It is preferable that the diffracted light is evaluated using the arrangement being near to the actual state and its embodiment is described later.

As described above, so far as the critical process only is concerned, in the processes of manufacturing the DRAM, in order from a lower layer, the field process, gate process, cell contact process, pit contact process, bit line process, capacitor contact process, and cylinder process are included. That is, the cell contact process includes a gate process (various kinds of implant processes intervene therebetween) and, as shown in FIG. 7, the gate 65 has its arrangement direction in the X direction (arrangement direction in the 0 degree direction) and has its repeating direction in the Y direction. The inspecting condition for the gate 65 is uniquely the condition for receiving diffracted light in the X direction (arrangement direction in the 0 degree direction). The use of illumination light having a wavelength and resist refractive index that receives only the signal (diffracted light) of a completely uppermost layer is ideal, however, in actuality, in some cases, the illumination light transmits through the lower layer and the inspection is influenced by the lower layer (signal). In some cases, the signal from the lower layer has doughnut-shaped luminance unevenness in images on the entire wafer and luminance unevenness occurs for every exposure shot. These phenomena including luminance unevenness occur more or less in all processes and, therefore, the non-defective wafer image A1 or inspection image A2 shown in FIG. 3 cannot avoid the influence of the occurrence of these phenomena. As a result, the inspection of defects with sufficient detection sensitivity becomes impossible. As the wafer becomes increasingly fine and minute, the resist thickness tends to be thin and it is no exaggeration to say that its lower layer is seen in a transparent manner.

Therefore, when the cell contact 70 is inspected, it is preferable that the inspecting condition for the arrangement direction in the 0 degree direction is avoided. Thus, the arrangement direction of the gate 65 existing in the lower layer is the X direction (arrangement direction in the 0 degree direction) and, therefore, by setting the inspecting condition so that the diffracted light having an angle being different from the above angle is received, the diffracted light from the gate 65 in the lower layer is not received, thus enabling the avoidance of the influence by the lower layer. As a result, the image of a non-defective wafer without luminance unevenness and inspected image can be obtained which enables great improvement of detection sensitivity. This means that, even when the resist becomes thin or when self layout is changed due to higher density, the inspection can be made according to optimum inspecting conditions.

Figure 33:
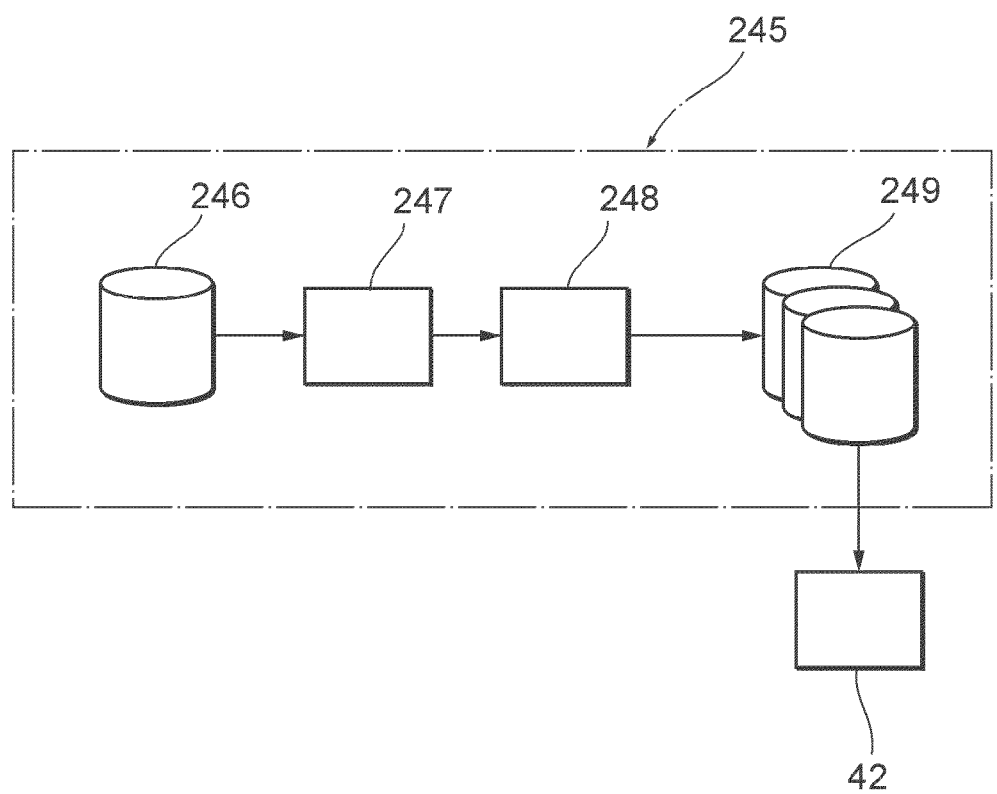
FIG. 33 is a control block diagram of an inspecting condition determining section of a modified example.

Next, a modified example of the inspecting condition determining section is described. The inspection determining section 245 of the modified example, as shown in FIG. 33, is made up of an arrangement data inputting section 246, an SEM image correcting section 247 connected electrically with the arrangement data inputting section 246, a CD value change/diffracted light simulator section 248 connected electrically with the SEM image correcting section 247, and an inspecting condition data outputting section 249 connected electrically with the CD value/change diffracted light simulator section 248.

Into the arrangement data inputting section 246 is inputted and stored design data (CAD data or the like) of a reticle as arrangement information. The reticle (not shown) is equivalent to an original plate used when a circuit pattern is exposed on the wafer 50 and a light-transmitted portion and light-shielded portion are formed on a glass plate so as to be four times larger in size than the size of a wafer. Moreover, the reticle is EB (Electron-Beam)-drawn based on the design data. However, in fine and minute patterns formed by the critical process, even if the pattern is rectangular on the reticle, the pattern, when being exposed on the wafer 50, becomes rectangular with rounded corners and, in many cases, elliptical. Furthermore, a square shape on the reticle becomes circular on the wafer. There are two reasons for that. The first reason is related to a problem of EB drawing resolution and/or etching accuracy at the time of the formation of the reticle and the second reason is related to an optical problem about aberrations in image formation and/or optical proximity correction at the time of exposure. Therefore, when design data of the reticle is used for the diffracted light simulation such as FFT processing, there is an alienation between design data of the reticle and data on the diffracted light from an actual wafer 50.

According to the present embodiment, two kinds of information described below is used. Firstly, macro values applied to CAD data (based on design coordinates) of the reticle are utilized. For example, in the cell contact process, the central coordinates of a hole, its arrangement direction, and values of pitches are used. The central coordinates of the hole, its arrangement direction, and values of pitches are not influenced by the accuracy of a reticle and image formation and, therefore, these values are used as they are.

Secondly, micro values applied to CD value measurement data obtained using the SEM (based on wafer measurement values) are used. That is, reticle accuracy, image formation accuracy, and CD values (including a taper and the like) that may be influenced in the process are used. These values are actually measured values including variations and, for example, in the cell contact process, actual states of long and short diameters of an elliptical hole can be reflected. In addition, information about a bottom, top, and depth is contained. However, if the actual measurement of the depth of a hole is difficult, a designed value is used instead.

As described above, macro values of the CAD data of the reticle are inputted, as arrangement data, to the arrangement data inputting section 246 and the SEM image correcting section 247 makes corrections to these macro values so as to come near to values of the pattern on the wafer 50. For example, the SEM image correcting section 247 uses a diameter of an upper surface (top) and a diameter of a bottom surface (bottom) as a long diameter and short diameter of an elliptic hole, based on the information obtained by measuring the cell contact hole using the SEM. This method is not limited to the cell contact hole. In the case of a DRAM, its resist is thicker compared with a flash memory or the like and, therefore, a hole has a comparatively large depth. As a result, as an unconscious case, there are some cases in which a hole has a tapered shape. For example, a cylinder has a large depth and is tapered accordingly. Even in the case of the cell contact, in some cases, its top diameter is 120 nm and its bottom diameter is 70 nm. Therefore, the SEM image correcting section 247 uses the information about diameters of the top and bottom of the hole as correcting information.

Furthermore, it is preferable to use, as information corresponding to CD tolerance values to be stipulated from viewpoints of process management, for example, SEM information about a CD value obtained at the time of best focus, CD value within the very possible tolerance, and CD value plainly out of tolerance. In the line and space pattern, from viewpoints of process management, a change in a line width presents a first problem at the time of the occurrence of defocus and, therefore, the CD value (top and bottom) obtained at the time is preferably used. Moreover, a factor of the CD value change caused by a change in film thickness may be considered as the additional factor.

As the CD value change/diffracted light simulator 248, "DiffractMOD" being an optical diffraction calculation engine manufactured by RSoft Design Group Corp. can be suitably used. The "DiffractMOD" allows an ellipse to be inputted as if a graphic is drawn and not only supports a tapered shape and three dimensional structure but also calculates diffracted light produced by swinging change factors such as a CD change and/or thickness change as a parameter. Naturally, a slanted incident state can be considered and, therefore, an arrangement direction being most sensitive to the CD value change, out of arrangement directions that can be selected, can be determined.

Figure 34:
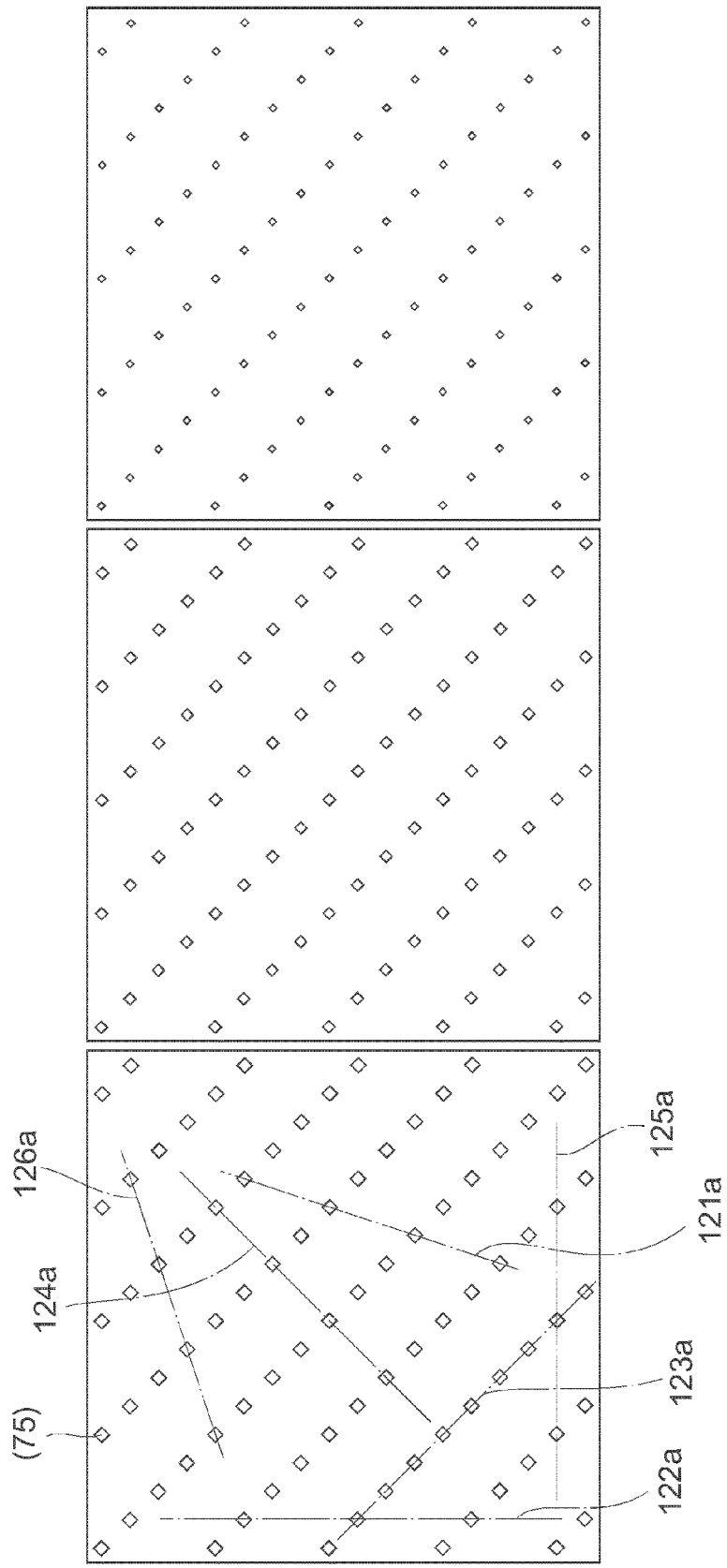
FIGS. 34A, 34B, and 34C are diagrams obtained by modeling a bit contact.

The method for determining conditions for inspection using such inspecting condition determining section 245 as described above is described by referring to FIGS. 34A, 34B, and 34C. FIG. 34A shows a bit contact model and the central coordinates or arrangement direction of the contact hole is obtained by calculating the CAD data of the reticle inputted into the arrangement data inputting section 246 and dimensions of the elliptical shape, depth, and tapered portion of the contact hole are obtained by being corrected by the SEM image correcting section 247 based on results from measurement using the SEM. FIG. 34A shows a model in a non-defective state. Further, as described above, the bit contact 75 has an arrangement direction 121*a* in the 0 degree direction, arrangement direction 122*a* in the 90 degree direction, arrangement direction 123*a* in the −45 degree direction, arrangement direction 124*a* in the 45 degree direction, arrangement direction 125*a* in the 72 degree direction, and arrangement direction 126*a* in the 18 degree direction.

FIG. 34B shows a model obtained by making a correction using the SEM image correcting section 247 based on results from the measurement by the SEM when CD values are changed within a tolerance range. That is, FIG. 34B is the model within the very possible tolerance.

FIG. 34C shows a model obtained by making a correction using the SEM image correcting section 247 based on results from the measurement by the SEM when CD values are changed greatly to a degree to which the CD values becomes out of the tolerance. That is, FIG. 34C shows a model being out of a range of tolerance.

Figure 35:
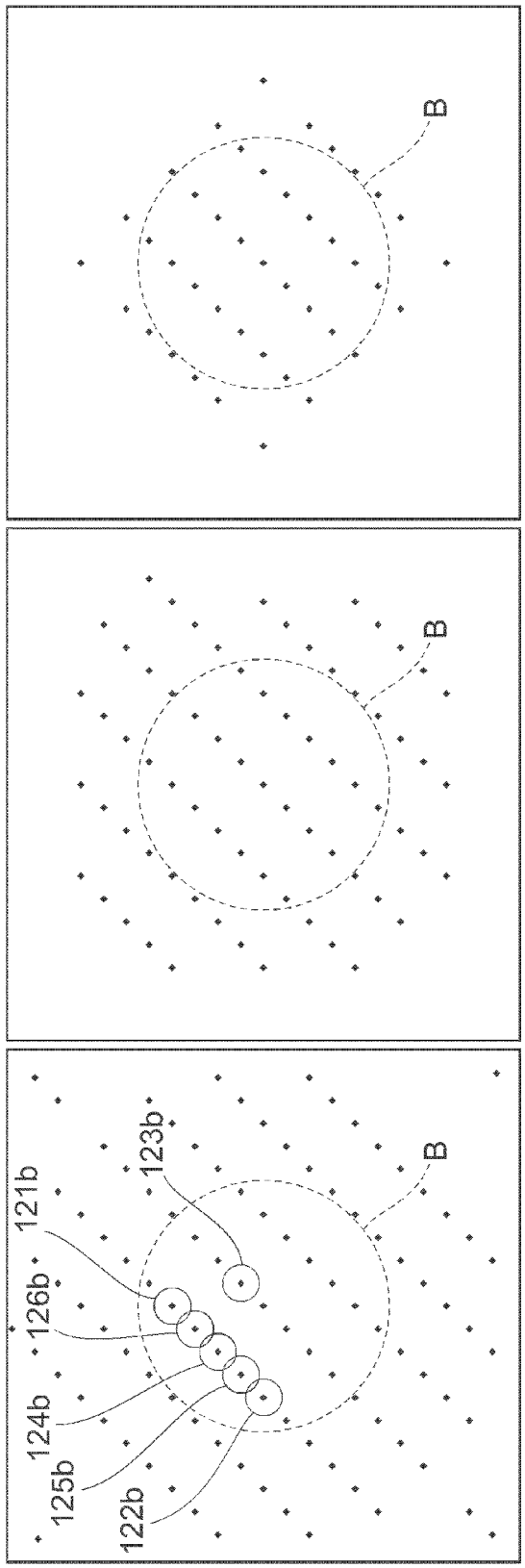
FIGS. 35A, 35B, and 35C are diagrams showing a result from FFT processing performed on the bit contact model.
Figure 36:
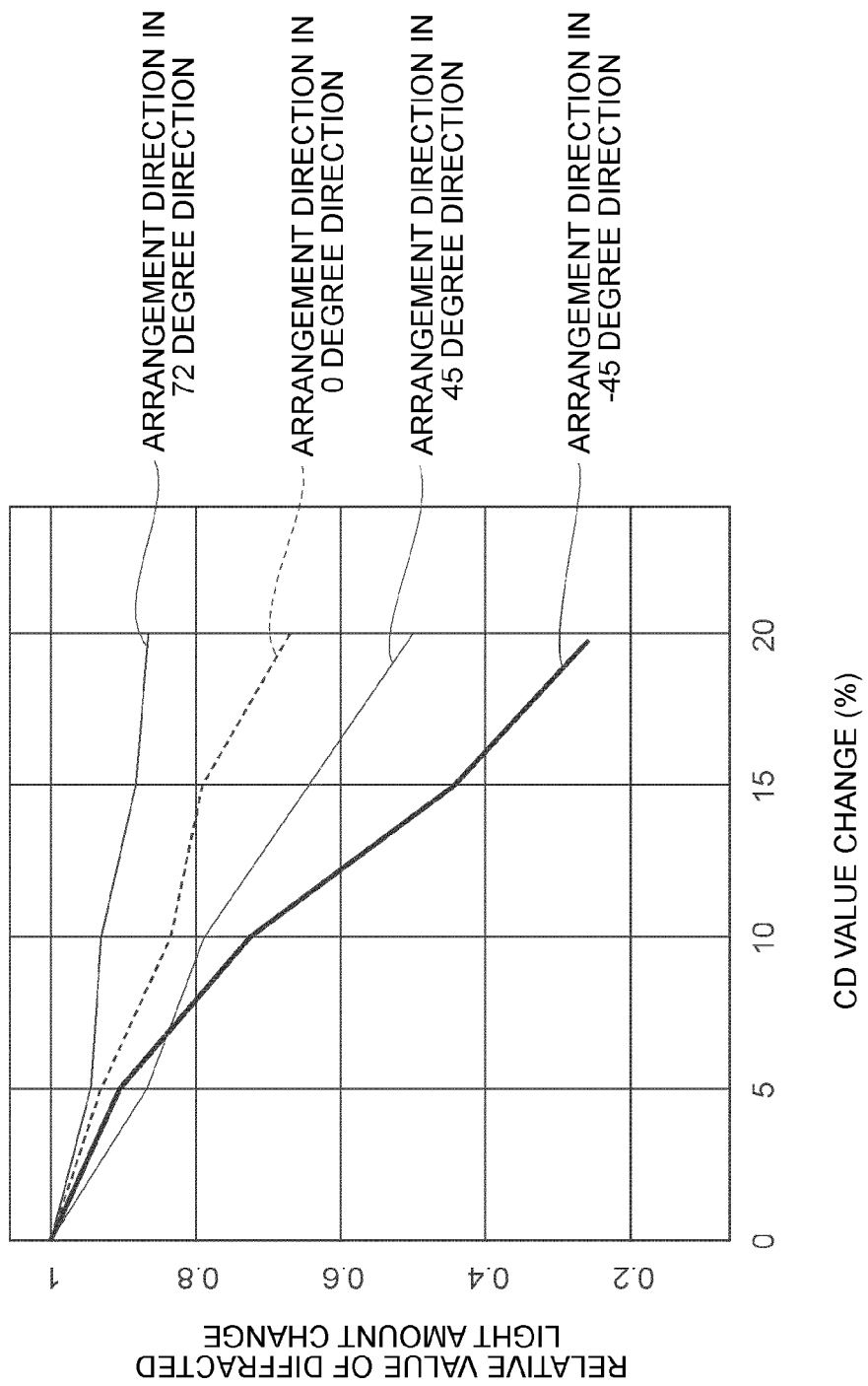
FIG. 36 is a graph showing a relation between a change in CD value and a change in an amount of diffracted light.

Next, when these models produced by the arrangement data inputting section 246 and SEM image correcting section 247 are evaluated by making the CD value change/diffracted light simulator section 248 perform FFT processing, results shown in FIGS. 35A, 35B, and 35C are obtained each corresponding respectively to FIGS. 34A, 34B, and 34C. Moreover, in FIG. 35A, rays of diffracted light 121*b* to 126*b* are displayed each corresponding respectively to the arrangement direction 121*a* in the 0 degree direction, arrangement direction 122*a* in the 90 degree direction, arrangement direction 123*a* in the −45 degree direction, arrangement direction 124*a* in the 45 degree direction, arrangement direction 125*a* in the 72 degree direction, and arrangement direction 126*a* in the 18 degree direction. FIG. 36 is a diagram obtained by evaluating the changes in amounts of diffracted light relative to the CD value change in the diffracted light corresponding to the arrangement direction 121*a* in the 0 degree direction, arrangement direction 123*a* in the −45 degree direction, arrangement direction 124*a* in the 45 degree direction, and arrangement direction 125*a* in the 72 degree direction.

FIG. 36 is a diagram showing changes of amounts of diffracted light relative to the CD change (in FIGS. 35B and 35C) with an amount of diffracted light in a non-defective mode in the case in FIG. 35A being set to be 1. The results show that the amount of diffracted light changes most sensitively to the CD value change in the arrangement direction in the −45 degree direction and the amount of diffracted light changes little in the arrangement direction in the 72 degree direction. The amount of diffracted light changes sensitively to the CD value change in order of the arrangement direction in the −45 degree direction, arrangement direction in the 45 degree direction, arrangement direction in the 0 degree direction, and arrangement direction in the 72 degree direction. That is, high detection sensitivity can be expected in this order. These results can be used as conditions for inspection.

When such evaluation as shown in FIGS. 35A, 35B, and 35C is performed by using the CD value change/diffracted light simulator section 248, it is preferable to use light having a plurality of selectable wavelengths $\lambda$, for example, an e-line ($\lambda$=546 nm), g-line ($\lambda$=436 nm), h-line ($\lambda$=405 nm), j-line ($\lambda$=313 nm) and light having a wavelength$\lambda$=about 250 nm for evaluation. As a result, the optimum wavelength and optimum azimuth angle can be determined. The inspecting condition is not necessarily one optimum condition and may be a plurality of conditions. The preferred degree may be converted into numbers as a score and, for example, in order of higher scores (most preferable level to slightly preferable level), the score may be contained in condition data for inspection.

For example, first two arrangement directions (arrangement direction in the −45 degree direction and arrangement direction in the 45 degree direction), out of four preferable arrangement directions, are used and a plurality of inspecting condition data is set so that two rays of light including j-line ($\lambda$=313 nm) and light ($\lambda$=near 250 nm) as illumination light and the condition data for inspection may be inputted from the inspecting condition data outputting section 249 to the inspecting condition setting section 42. By performing the inspection of the bit contact according to a plurality of conditions for inspection and by judging that the wafer 50 to be inspected has a defect when even one result shows the existence of the detect out of inspection results obtained from a plurality of conditions for inspection, a failure of detecting defects is decreased and detection reliability can be improved. Moreover, as described above, by selecting an arrangement direction being different from the arrangement direction of a lower layer, signals from the lower layer can be excluded. To realize the exclusion, weights can be assigned to the arrangement direction. That is, if there is an arrangement direction from which a relation with the lower layer is desired to be excluded, by considering and adding the information about the above arrangement direction to evaluation results by the diffracted light simulator section 248 to produce the inspecting condition data.

Furthermore, according to the inspecting condition determining section 245 of the modified example, the setting of inspecting conditions without using the wafer (waferless inspecting condition setting) is made possible. More concretely, the inspecting condition setting as an initial recipe is made possible by obtaining arrangement information (arrangement direction and repeating pitch) stored in CAD data or the like from the outside (office or the like) before the test on a wafer by a surface inspecting apparatus in a clean room and by performing evaluation using the CD value change/diffracted light simulator section 248. Particularly, at the first stage of development of a new product, under the nominal purpose of proposal conditions including the proposal of conditions for exposure and/or proposal of conditions for a process apparatus, the measurement of CD values using the SEM is frequently made, however, it is after such proposal of conditions that the inspection of wafers to be manufactured in quantity is required. However, the start of mass production of the wafer has to be realized at an early stage and the condition setting for the inspection for mass production wafer has to be performed for a short period. For this purpose also, the waferless inspecting condition setting is effective. Moreover, within a period of the condition proposal, measurement data of CD values using the SEM is accumulated gradually, thus improving the accuracy of evaluation by simulation.

In the present invention, the inspection is performed on the bit contact 75, however, the present invention is not limited to this and is effective not only in the cell contact 70 but also the capacitor contact 85 or cylinder 90 and further effective for the inspecting condition setting in the field process shown in FIG. 6. In FIG. 6, it is easily understood from the arrangement that a large amount of diffracted light may be obtained in the arrangement direction 62*a* in the 72 degree direction, however, it is not clear whether diffracted light occurs in the repeating arrangement other than the arrangement direction described above.

Figure 37:
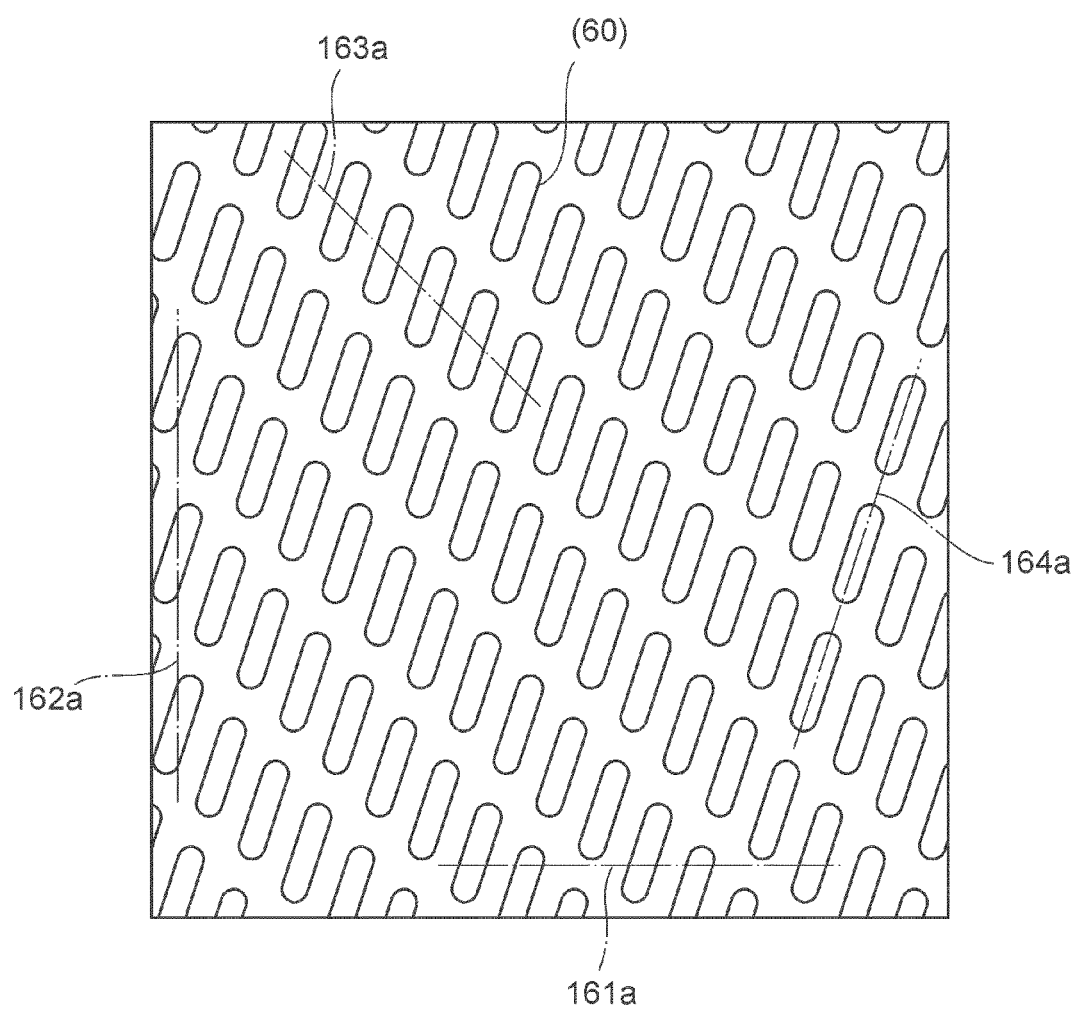
FIG. 37 is a diagram obtained by modeling a field process.

FIG. 37 is a diagram obtained by modeling the field process in FIG. 6. It is understood from FIG. 37 that the active area 60 has the arrangement direction 161*a* in the 0 degree direction, arrangement direction 162*a* in the 90 degree direction, arrangement direction 163*a* in the −45 degree direction, and arrangement direction 164*a* in the 72 degree direction.

Figure 38:
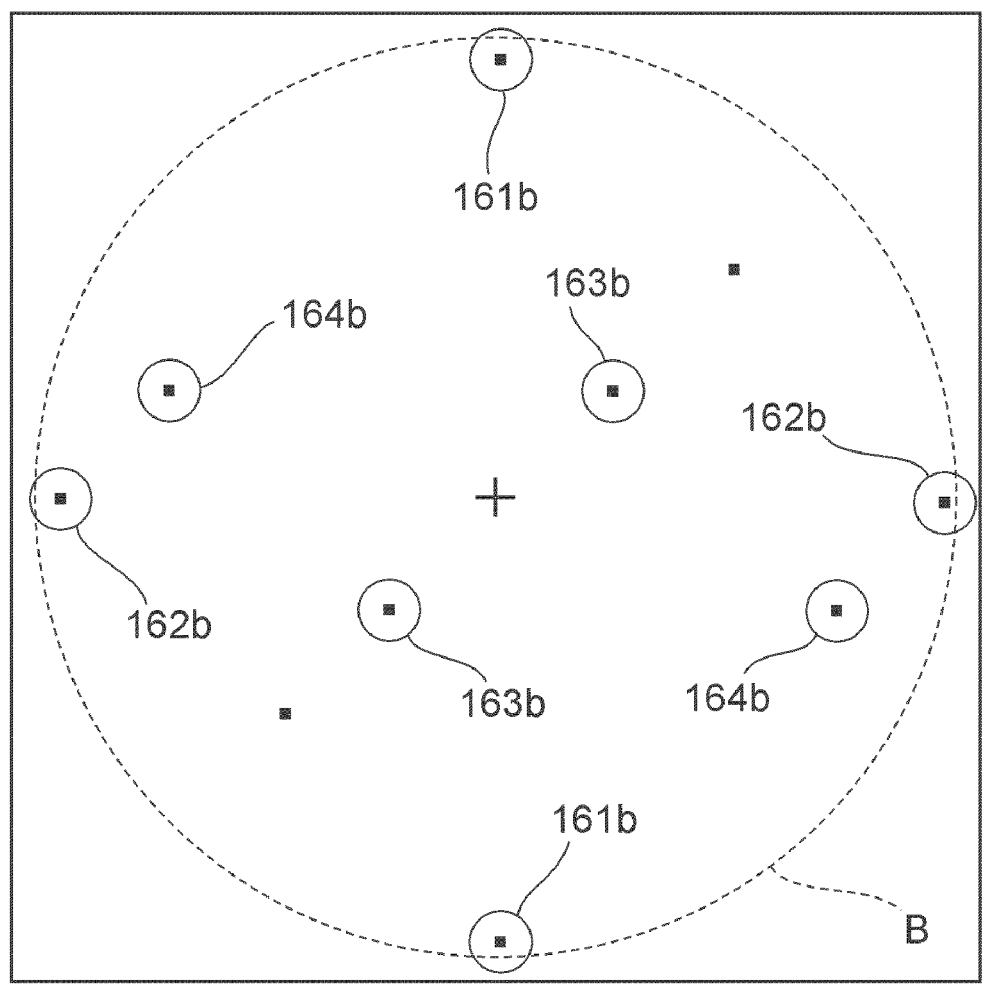
FIG. 38 is diagram showing a result from FFT processing performed on the model in FIG. 37.

FIG. 38 is a diagram obtained by performing FFT processing on the model in FIG. 37 using the CD value change/diffracted light simulator section 248 and by displaying a region near to its point of origin in an enlarged manner. In FIG. 38, rays of diffracted light 161*b* to 164*b* are displayed each corresponding respectively to the arrangement direction 161*a* in the 0 degree direction, arrangement direction 162*a* in the 90 degree direction, arrangement direction 163*a* in the −45 degree direction, and arrangement direction 164*a* in the 72 degree direction. As is apparent from FIG. 38, each of the rays of diffracted light 161*b* to 164*b* corresponding to four arrangement directions is within the diffracted light receiving range B. It is also understood that the 1st order diffracted light and 2nd order diffracted light corresponding to the arrangement direction in the −45 degree direction are within the diffracted light receiving range B.

Conditions, out of above conditions, being sensitive to the CD value change can be selected in the same ways as above by using the CD value change/diffracted light simulator 248. In the above methods, simulation is preferably performed in a manner to be suitably applied to the CD value change liable to occur at time of exposure and to the CD value change desired to be severely controlled. For example, when the CD value change in the long diameter direction of the active area 60 is desired to be severely managed compared with the CD value change in the short diameter direction of the active area 60, the azimuth condition in which the amount of diffracted light changes in a manner to be sensitive to the CD value change in the long diameter direction is preferably found out.

Or, by fabricating an FEM wafer in the field process and by obtaining wafer images according to a plurality of diffracted light receiving conditions, the inspecting conditions being sensitive to defocus may be determined. Even in the case of the bit contact described before, the same procedures may be selected.

In addition, in the embodiment described above, the case is described by using the DRAM as an example, however, the present invention is not limited to these and can be applied to other semiconductor devices such as a flash memory.

Figure 39:
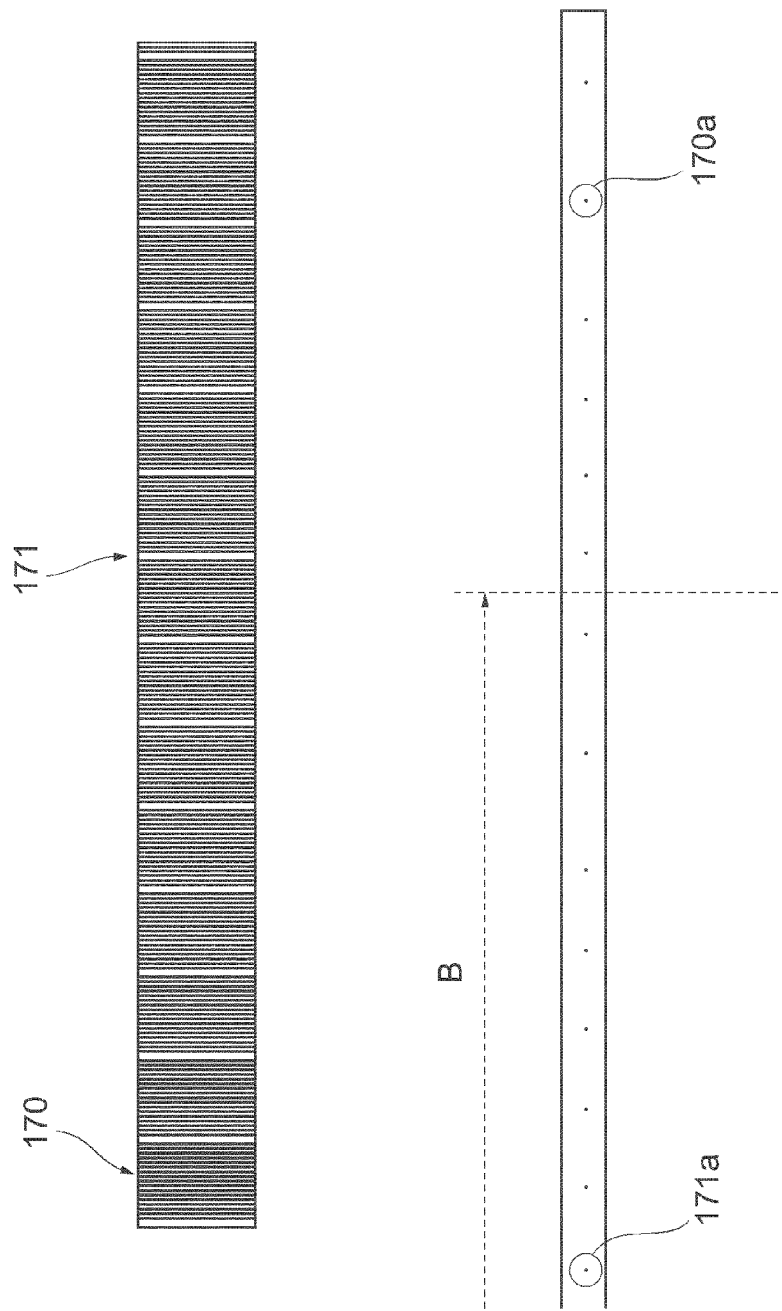
FIGS. 39A and 39B are schematic diagrams showing a gate process of a flash memory.

Next, the gate process of a NAND-type flash memory is described by referring to FIGS. 39A and 39B. In the gate process of the flash memory, as shown in FIG. 39A, 16 pieces of control gates 170 and a select gate 171 are disposed among the control gates 170. FIG. 39B shows an FET image which corresponds to the above disposition. In a leading-edge flash memory, F=40 to 50 nm and diffracted light 170*a* from the control gate 170 having a 2F pitch is out of the diffracted light receiving range B. However, (1st order) diffracted light 171*a* and higher order diffracted light, as shown in FIG. 39B, exist within the diffracted light receiving range B. Out of these rays of diffracted light, the diffracted light being most sensitive to the CD value change can be determined by the same way as described. Moreover, a NOR-type flash memory has a layout different from the NAND-type flash memory, however, by the same ways as described above, inspecting conditions being sensitive to the CD value change can be set.

Figure 40:
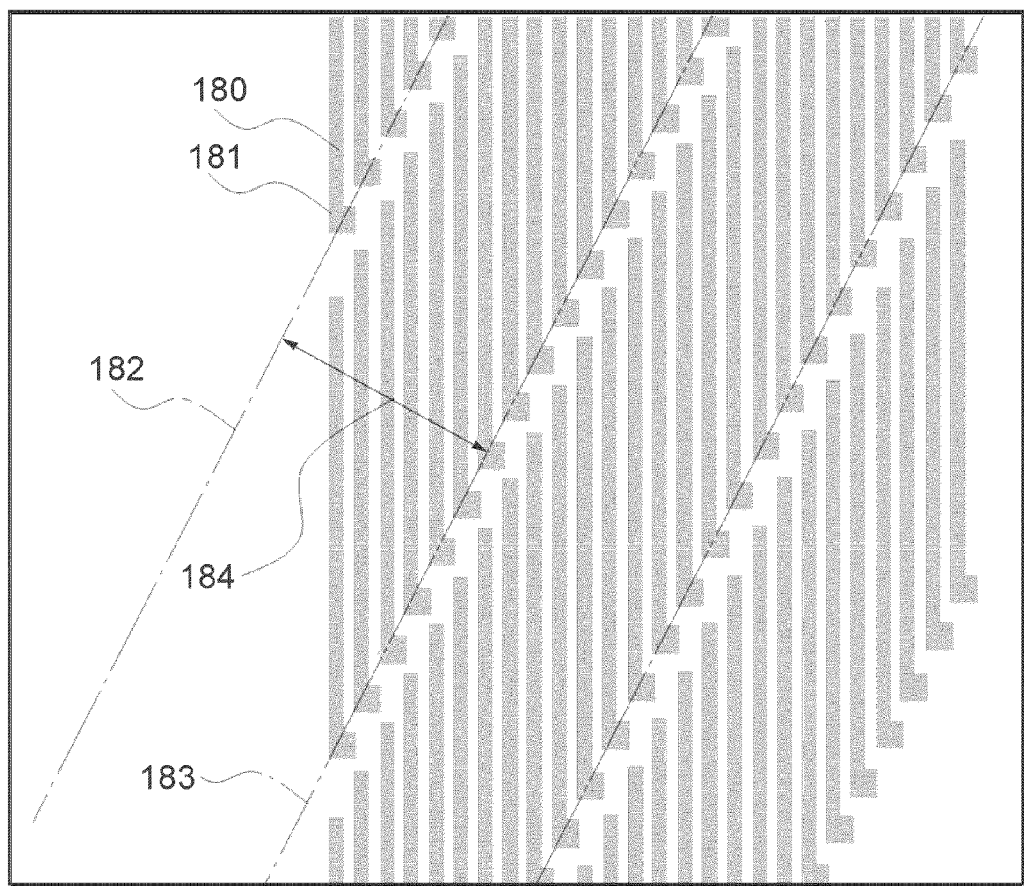
FIG. 40 is a schematic diagram showing a gate line of a flash memory.

As shown in FIG. 40, a gate line drawing portion 181 is disposed, without exception, at an end of the gate line 180 of the NAND-type flash memory. The gate line drawing portion 181 has a shape like a head of a golf club being larger than a line width of the gate line 180 and is so configured as to keep contact with higher layers. Therefore, the gate line drawing portion 181 has an arrangement being slanted relative to the repeating arrangement direction of the gate line 180 and the repeating direction of each of the arrangements 182 and 183 is also slanted relative to the repeating arrangement direction of the gate line 180. The gate line drawing portion 181 is not a contact hole, however, sine the arrangements 182 and 183 of the gate line drawing portion 181 are made slanted relative to the repeating arrangement direction of the gate line 180, as if the arrangement is an arrangement of the above-described contact hole, diffracted light can be obtained at the pitch of a repeating cycle 184 of each of the arrangements 182 and 183.

Furthermore, in an exposure machine, priority is given to repeatability of the gate line 180 to be exposed and optimization is performed on a phase-shifting method and a modified illumination method. Therefore, when an error such as defocus occurs in the exposure machine, a pattern being isolated from the gate line 180 is easily affected by the defocus and a defect such as pattern falling is liable to occur in the gate line drawing section 181 rather than the gate line 180. Thus, in the surface inspecting apparatus of the present invention, sensitive detection of defects in not only the gate line 180 but also the gate line drawing section 181 is necessary. To achieve this, the setting of diffraction conditions is preferred so that diffracted light corresponding to the repeating cycle 184 of each of the arrangements 182 and 183 can be obtained and a wafer can be rotated and the CD value change can be detected sensitively. Even in such processes of semiconductor production as described above, it is possible to avoid an influence by a backing caused by a difference in the azimuth angle of diffracted light (arrangement direction of patterns).

In a logic device, though its repeating arrangement region area ratio in a semiconductor chip is small, unlike various memories, the inspection of defects using diffracted light has been applied. However, even in the same manufacturing process, since arrangement directions of patterns and repeating pitches corresponding to a plurality of arrangement regions exist, it was difficult to determine inspecting conditions corresponding to each of arrangement directions. Unlike the conventional technology, according to the present invention, diffraction simulation using the arrangement CAD data is possible and, therefore, easy determination of inspecting conditions is realized.

Additionally, the defect inspection of the present invention can be applied not only to semiconductor wafers but also to products having a repeating arrangement pattern such as a reticle. It has been already described that the reticle pattern is drawn based on designing data and, according to EB drawing accuracy, even if the pattern is of a rectangle shape according to a viewpoint of designing, the reticle pattern actually comes to be round. The present invention can be applied to the inspection of the degree of roundness of an object to be inspected. That is, the technology of the present invention can be easily understood by thinking in a manner in which the CD value change is replaced with the degree of roundness of a reticle pattern, change in a rectangular change, change in line width or the like. By evaluating the arrangement direction and/or repeating pitch being sensitive to these changes and by setting the arrangement direction and/or repeating pitch as inspecting conditions, a product having a shape (roundness) change in the pattern of the reticle or large dimensional changes can be detected as a defect.

EXPLANATION OF NUMERALS AND CHARACTERS

1: Surface inspecting apparatus, 20: Illuminating section, 25: Illumination light, 30: Detecting section, 35: Diffracted light, 40: Image processing section, 41: Inspecting section, 42: Inspecting condition setting section, 43: FEM evaluating section, 45: Inspecting condition determining section, 50: Wafer (semiconductor substrate), 60: Active area (hole pattern), 65: Gate (line pattern), 70: Cell contact (hole pattern), 75: Bit contact (hole pattern), 80: Bit line (line pattern), 85: Capacitor contact (hole pattern), 90: Cylinder (hole pattern), 245: Inspecting condition determining section (modified example)

What is claimed is:

1. A surface inspecting method for inspecting a surface of a semiconductor substrate having a line pattern and a hole pattern formed on the line pattern, each being arranged repeatedly, comprising:
    setting an irradiating direction of illumination light to be applied to a surface of the semiconductor substrate;
    irradiating the surface of the semiconductor substrate with illumination light in the irradiating direction;
    detecting diffracted light corresponding to a pitch of the hole pattern from the surface irradiated with the illumination light; and
    judging existence/non-existence of a defect occurring in the hole pattern based on the detected diffracted light;
    wherein, the irradiating direction is set so that the irradiating direction of the illumination light on the surface of the semiconductor substrate is different from a repeating arrangement direction of the line pattern and substantially matches a repeating arrangement direction of the hole pattern.

2. The surface inspecting method according to claim 1, wherein the irradiating direction is set so that the irradiating direction of the illumination light on the surface of the semiconductor substrate is different from the repeating arrangement direction of the line pattern and the diffracted light an amount of which greatly changes depending on a change in a shape of the hole pattern occurs.

3. The surface inspecting method according to claim 2, wherein the irradiating direction is set by performing simulation of a change in an amount of the diffracted light according to a change in shape of the hole pattern based on designing information of the hole pattern or shape measurement information of a hole pattern whose shape has been measured in advance.

4. A surface inspecting method for inspecting a surface of a semiconductor substrate having a hole pattern, comprising:
    setting an irradiating direction of an illumination light to be applied to a surface of the semiconductor substrate;
    irradiating the surface of the semiconductor substrate with illumination light in the irradiating direction;
    detecting diffracted light from the surface irradiated with the illumination light, the diffracted light corresponding to a pitch of the hole pattern; and
    judging existence/non-existence of a defect in the hole pattern based on the detected diffracted light,
    wherein the irradiating direction is set by performing simulation of a change in an amount of diffracted light according to a change in shape of the hole pattern so that the diffracted light an amount of which changes greatly according to a change in shape of the hole pattern occurs.

5. The surface inspecting method according to claim 4, wherein simulation of a change in an amount of the diffracted light is performed according to a change in shape of the hole pattern based on one of designing information about the hole pattern and shape measurement information about a hole pattern whose shape has been measured in advance.

6. The surface inspecting method according to claim 4, wherein the irradiating direction is set so that the diffracted light an amount of which changes greatly according to a change in shape of the hole pattern occurs and that diffracted light is not easily produced form a layer on a side being lower than the hole pattern.

7. A surface inspecting apparatus for inspecting a surface of a semiconductor substrate having a line pattern and a hole pattern formed on the line pattern, comprising:
    a setting section to set an irradiating direction of illumination light to be applied to a surface of the semiconductor substrate;
    an illuminating section to irradiate the surface of the semiconductor substrate with illumination light the irradiating direction set by the setting section;
    a detecting section to detect diffracted light corresponding to a pitch of the hole pattern from the surface irradiated with the illumination light; and an inspecting which judges existence/non-existence of a defect occurring in the hole pattern based on the diffracted light detected by the inspecting section, the setting section setting the irradiating direction so that the irradiating direction of the illumination light on the surface of the semiconductor substrate is different from a repeating arrangement direction of the line pattern and substantially matches a repeating arrangement direction of the hole pattern.

8. The surface inspecting apparatus according to claim 7, wherein the setting section sets the irradiating direction so that the irradiating direction of the illumination light on the surface of the semiconductor substrate is different from the repeating arrangement direction of the line pattern and the diffracted light an amount of which greatly changes depending on a change in a shape of the hole pattern occurs.

9. The surface inspecting apparatus according to claim 8, wherein the setting section sets the irradiating direction by performing simulation of a change in an amount of the diffracted light according to a change in shape of the hole pattern based on one of designing information about the hole pattern and shape measurement information about a hole pattern whose shape has been measured in advance.

10. A surface inspecting apparatus for inspecting a surface of a semiconductor substrate having a hole pattern, comprising:

a setting section to set an irradiating direction of an illumination light to be applied to a surface of the semiconductor substrate;

an illuminating section to irradiate the surface of the semiconductor substrate with illumination light in the irradiating direction set by the setting section;

a detecting section to detect diffracted light from the surface irradiated with the illumination light, the diffracted light corresponding to a pitch of the hole pattern; and an inspecting section to judge existence/non-existence of a defect in the hole pattern based on the diffracted light detected by the detecting section, the setting section setting the irradiating direction by performing simulation of a change in an amount of diffracted light according to a change in shape of the hole pattern so that the diffracted light an amount of which changes greatly according to a change in shape of the hole pattern occurs.

11. The surface inspecting apparatus according to claim 10, wherein the setting section performs simulation of a change in an amount of the diffracted light according to a change in shape of the hole pattern based on one of designing information about the hole pattern and shape measurement information about a hole pattern whose shape has been measured in advance.

12. The surface inspecting apparatus according to claim 10, wherein the setting section sets the irradiating direction so that the diffracted light an amount of which changes greatly according to a change in shape of the hole pattern occurs and that diffracted light is not easily produced form a layer on a side being lower than the hole pattern.

13. The surface inspecting method according to claim 5, wherein the irradiating direction is set so that the diffracted light an amount of which changes greatly according to a change in shape of the hole pattern occurs and that diffracted light is not easily produced form a layer on a side being lower than the hole pattern.

14. The surface inspecting apparatus according to claim 11, wherein the setting section sets the irradiating direction so that the diffracted light an amount of which changes greatly according to a change in shape of the hole pattern occurs and that diffracted light is not easily produced form a layer on a side being lower than the hole pattern.

15. A surface inspecting method for inspecting a surface of a semiconductor substrate having periodic patterns disposed on an under layer with a predetermined period and a plurality of hole patterns formed on the periodic patterns, comprising:

setting an irradiating direction of illumination light to be applied to a surface of the semiconductor substrate;

irradiating the surface of the semiconductor substrate with illumination light in the irradiating direction;

detecting diffracted light emitted from the hole patterns from the surface irradiated with the illumination light; and judging existence/non-existence of a defect occurring in the hole patterns based on the detected diffracted light, wherein the irradiating direction is set so that the irradiating direction of the illumination light on the surface of the semiconductor substrate is different from a periodic direction of each of the periodic patterns and substantially matches a repeating arrangement direction of each of the hole patterns.

16. The surface inspecting method according to claim 15, wherein the irradiating direction is set so that the irradiating direction of the illumination light on the surface of the semiconductor substrate is different from the periodic direction of each of the periodic patterns and the diffracted light an amount of which greatly changes depending on a change in a shape of each of the hole patterns is produced.

17. The surface inspecting method according to claim 16, wherein the irradiating direction is set by performing simulation of a change in an amount of the diffracted light according to a change in shape of each of the hole patterns based on one of designing information about each of the hole patterns and shape measurement information about each of the hole patterns whose shape has been measured in advance.

18. A surface inspecting apparatus for inspecting a surface of a semiconductor substrate having periodic patterns disposed on an under layer with a predetermined period and a plurality of hole patterns formed on the periodic patterns, comprising:

a setting section to set an irradiating direction of an illumination light to be applied to a surface of the semiconductor substrate;

an illuminating section to irradiate the surface of the semiconductor substrate with illumination light in the irradiating direction set by the setting section;

a detecting section to detect diffracted light from the surface irradiated with the illumination light; and an inspecting section to judge existence/non-existence of a defect in each of the hole patterns based on the diffracted light detected by the detecting section, wherein the setting section sets the irradiating direction so that the irradiating direction of the illumination light on the surface of the semiconductor substrate is different from a periodic direction of each of the periodic patterns and substantially matches a repeating arrangement direction of each of the hole patterns.

19. The surface inspecting apparatus according to claim 18, wherein the setting section sets the irradiating direction so that the irradiating direction of the illumination light on the surface of the semiconductor substrate is different from the periodic direction of each of the periodic patterns and the diffracted light an amount of which greatly changes depending on a change in a shape of each of the hole patterns is produced.

20. The surface inspecting apparatus according to claim 19, wherein the setting section sets the irradiating direction by performing simulation of a change in an amount of the diffracted light according to a change in shape of each of the hole patterns based on one of designing information about each of the hole patterns and shape measurement information about each of the hole patterns whose shape has been measured in advance.

* * * * *